US006905714B2

(12) United States Patent
Ong et al.

(10) Patent No.: US 6,905,714 B2
(45) Date of Patent: Jun. 14, 2005

(54) METHOD FOR MODULATING STEROIDOGENIC ACTIVITY

(75) Inventors: Yek Cheng Ong, Singapore (SG); Eu Leong Yong, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 09/793,772

(22) Filed: Feb. 27, 2001

(65) Prior Publication Data

US 2001/0046524 A1 Nov. 29, 2001

Related U.S. Application Data

(60) Provisional application No. 60/185,757, filed on Feb. 29, 2000.

(51) Int. Cl.[7] ............................. A61K 35/78; C12N 1/10
(52) U.S. Cl. ........................................ 424/769; 435/810
(58) Field of Search ................................ 424/769, 725; 435/497, 810, 947, 975

(56) References Cited

U.S. PATENT DOCUMENTS 6,017,924 A * 1/2000 Edwards et al.

FOREIGN PATENT DOCUMENTS

| JP | 04169536 | | 6/1992 |
| JP | 041487623 | * | 7/1992 |
| JP | 05268921 | * | 10/1993 |

OTHER PUBLICATIONS

D.J. Mabberley, The Plant Book, Second Edition, 1997. Cambridge University Press, The United Kingdom, unnumbered page.*

Megn et al. Zhongcaoyao (1994), 25(7): 350–2. Comparative analysis on the quality betweeh original and regenerated barks of Euccomia ulmoides (Abstract).*
Ren et al. Khim. Farm. Zh. (22, No. 10: 1236–41). Antiatherosclerotic properties of medicinal plants (Abstract).*
Qu, Gang–Jian et al., Taiyoku Kagaku, 48(4): 501–508. Effects of Tu–Chung extract administration serum testosterone in hind limb–suspended rats. (Translated).*
G. Jenster et al., Proc. Natl. Acad. Sci. USA, vol. 94, pp. 7879–7884, Jul. 1997.
Y. Li et al., Biol. Pharm. Bull., 22(6) 582–585 (1999).
Y. Li et al., Biol. Pharm. Bull., 22(9) 941–946 (1999).
E. L. Yong et al., Molecular and Cellular Endocrinology, 137 (1998) 41–50.
J. Lim et al., Molecular and Cellular Endocrinology, 131 (1997) 205–210.
T. G. Tut et al., Journal of Clinical Endocrinology and Metabolism, vol. 82, No. 11, pp. 3777–3782 (1997).
A. T. Dowsing et al., The Lancet, vol. 354, pp. 640–643 (Aug. 21, 1999).
Y. C. Ong et al., The Lancet, vol. 354, pp. 1444–1445 (Oct. 23, 1999).
Q. Wang et al., Clin. Genet. vol. 54. pp. 185–192 (1998).
Ghadessy et al., Journal of Clinical Investigation, vol. 103, No. 11, pp. 1517–1525, Jun. 1999.
E.L. Yong et al. The Lancet, vol. 344, pp. 826–827 (Sep. 17, 1994).
Qu–Gang–Jian et al., Japanese Journal of Physical Fitness and Sports Medicine, vol. 46, No. 3, 1997, pp. 263–272, abstract only.
Qu, Gang–Jian et al., Tairyoku Kagaku, vol. 48, No. 4, Aug. 1999, pp. 501–508, abstract only.
Metori Koichi et al., Biological & Pharmaceutical Bulletin, vol. 17, No. 7, 1994, pp. 917–920, abstract only.

* cited by examiner

Primary Examiner—Christopher R. Tate
Assistant Examiner—Michele C. Flood
(74) Attorney, Agent, or Firm—Birch, Stewart, Kolasch & Birch, LLP

(57) ABSTRACT

The present invention relates generally to a method for modulating steroidogenic activity and a composition useful for same. The present invention further relates to a composition comprising a steroidogenic modulator useful for modulating physiological processes mediated by the androgen receptor or an active form thereof or complex comprising same and/or for modulating physiological processes mediated by estrogen receptors. The composition of the present invention preferably comprises an extract of herbs or botanical or horticultural equivalents of the herbs or chemical or functional equivalents of one or more components of the herbal extract thereof.

18 Claims, 17 Drawing Sheets

Lane 1. Control
Lane 2. Testosterone alone (5000ug)
Lane 3. Testosterone (5000ug) + Ethanolic EU extract (50mg dry weight)

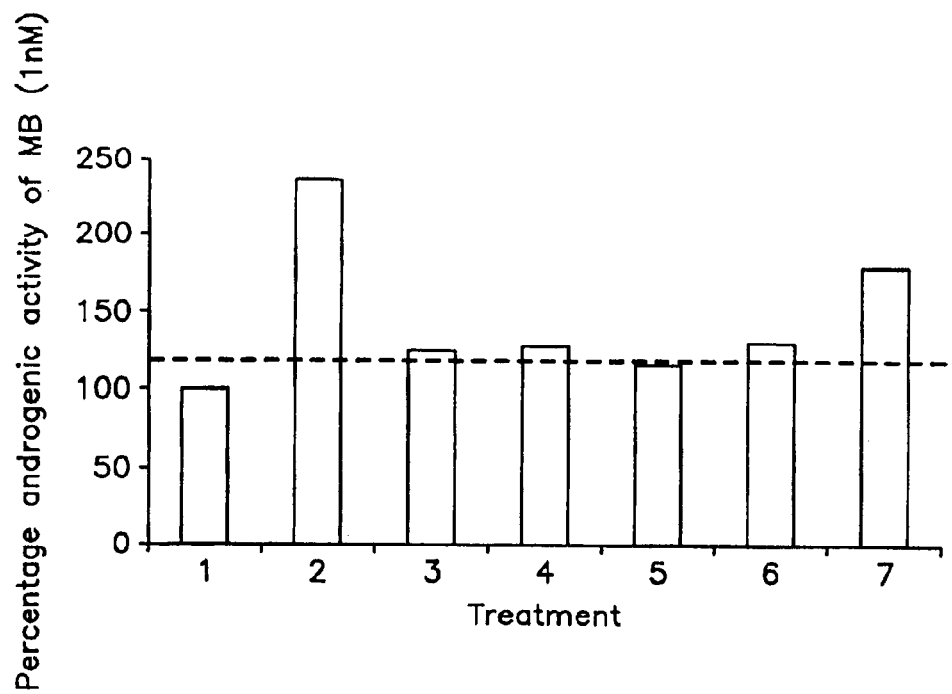

FIG.7A

Lane 1. MB (1nM)
Lane 2. Ethanolic EU extract (60 ng dry weight/ml treatment medium) + MB (1nM)
Lane 3. Ethanolic EU extract (~60 ng dry weight/ml treatment medium) reconstituted from individual Diol matrix fractions (lane4 – lane 7)
Lane 4. Hexane 100% Diol matrix fraction + MB (1nM)
Lane 5. Hexane:DCM (1:1) 100% Diol matrix fraction + MB (1nM)
Lane 6. DCM 100% Diol matrix fraction + MB (1nM)
Lane 7. MeOH 100% Diol matrix fraction + MB (1nM)

Lane 1. DHT (10nM)
Lane 2. DCM 100% Diol matrix fraction + DHT (10nM)
Lane 3. Ethyl acetate 100% Diol matrix fraction + DHT (10nM)
Lane 4. EtOH I Diol matrix fraction + DHT (10nM)
Lane 5. EtOH II Diol matrix fraction + DHT (10nM)

METHOD FOR MODULATING STEROIDOGENIC ACTIVITY

This Application claims benefit of 60/185,757 Feb. 29, 2000.

FIELD OF THE INVENTION

The present invention relates generally to a method for modulating steroidogenic activity and a composition useful for same. The present invention further relates to a composition comprising a steroidogenic modulator useful for modulating physiological processes mediated by the estrogenic or androgenic receptor or an active form thereof or complex comprising same and/or for modulating physiological processes mediated by the estrogen and androgen receptors. The composition of the present invention preferably comprises an extract of herbs or botanical or horticultural equivalents of the herbs or chemical or functional equivalents of one or more components of the herbal extract.

BACKGROUND OF THE INVENTION

Bibliographic details of the publications referred to by author in this specification are collected at the end of the description.

Herbal formulations comprising extracts of more than one herbal plant have been used for centuries in Traditional Chinese Medicine (TCM). There is now an increasing acceptance of their value and therapeutic efficacy in Western medicine. TCM has its own unique and philosophical theory in etiology, pathology, diagnosis, pharmacology and therapeutics. Many concepts surrounding TCM have particular relevance to Western medicine such as viewing parts of the body as an organic whole, considering inter-relations and influences between organs and being aware of relevant adaptation of the human body to the natural environment.

Despite the effectiveness of many herbal formulations in the treatment of a range of conditions, little is known about how the formulations work. Information on the mechanisms of action for herbal formulations would permit the rational design of particular compositions or chemical synthetic production of one or more components of the compositions as well as ensuring that the appropriate composition is selected for a particular ailment or condition.

Androgens are one of a group of steroid hormones which include testosterone and dihydrotestosterone (DHT). The androgens stimulate the development of male sex organs and male secondary sexual characteristics such as beard growth, deepening of the voice and muscle development. The principal source of these hormones is the testis but they are also secreted in small amounts from the adrenal cortex.

Androgens act through an X-linked androgen receptor (AR) to regulate androgen-responsive genes. This in turn leads to a cascade of metabolic events which manifest as androgenic effects including male sexual development in the fetus, secondary sexual development and sperm production at puberty, anabolic processes including muscle growth and bone density, male sex drive (i.e. libido), hair growth, skin condition, and physical stamina in adults (Wilson, 1992).

Naturally occurring and synthetic androgens are used in replacement therapy such as to treat delayed puberty in boys, hypogonadal men, impotence and as anabolic agents and in the treatment of cancer. However, only limited number of natural and synthetic androgens are known. As stated above, testosterone and DHT are examples of natural androgens. Miborelone and mesterolone are examples of synthetic androgens. The chemical structure common to steroidal hormones, including androgens, is the 1,3-cyclopentanophrenanthrene ring system.

Androgens in the cell bind to the ligand-binding domain (LBD) of the androgen receptor. Upon ligand binding, the androgen receptor which comprises the transactivation domain (TAD), DNA-binding domain (DBD) and the ligand bound LBD adopts a transactivational conformation and translocates to the nucleus where it binds specifically to the androgen-responsive element (ARE) of the androgen-regulated gene. Following the recruitment of DNA polymerase and co-activators to form the quaternary transcription complex, the gene downstream of the ARE is expressed. Hence, the prerequisite of androgen receptor activity is the specific binding of a ligand into the hydrophobic core of the androgen receptor LBD.

As stated above, there are many conditions associated with low androgen levels, hypofunction of the androgen receptor (Yong, 1994; Tut, 1997; Lim, 1997; Yong, 1998; Wang, 1998, Ghadessy, 1999; Ong, 1999; Dowsing, 1999), declining androgen action associated with aging and other conditions.

There is a need to identify naturally occurring compounds and materials generally from non-mammalian sources, which interact with or activate the androgen receptor and/or the androgen-androgen receptor complex leading to transcription of an androgen-responsive gene. There is also a need to identify estrogenic modulating agents, as well as agents modulating the effects of other members of the steroid/nuclear receptor superfamily of proteins. The identification of such compounds and molecules is needed for the development of therapeutic compositions and/or nutraceutic applications.

In work leading up to the present invention, the inventors sought an edible plant extract with steroidogenic properties.

*Eucommia Ulmoides* OLIVER (Du-Zhong) is a large deciduous tree which originated in China. The bark of the tree (commonly referred to as Cortex eucommiae) has been used for natural medicine since ancient times (Wei, 1955; Li, 1987).

Decoctions of *E. Ulmoides* (EU) bark have been used for, amongst other things, the relief of back pain, to increase strength, to make bones and muscle strong, to increase recovery from fatigue, to increase ability to remember and to induce an anti-aging effect. Mechanical training and the use of EU leaf extracts co-operatively can increase the ability of rats to avoid lactate accumulation in skeletal muscle and the administration of the EU leaf extract along with light intensity training enhances the ability of a muscle to resist fatigue (Li, 1996b). EU leaves contain compounds similar to the bark and are reported to have similar pharmacological effects. Since irridoid monoglycosides, such as geniposidic acid and aucubin in EU can stimulate collagen synthesis in aged model rats (Li, 1991a), it is thought that the active compound is actually geniposidic acid or aucubin.

Crude extracts of Tochu tea, an aqueous extract of EU leaves, have a suppressing effect on the induction of chromosome aberrations in CHO cells and mice. Out of 17 Tochu tea components, five irridoids (geniposidic acid, geniposide, asperulosidic acid, deacetyl asperulosidic acid and asperuloside) and three phenols (pyrogallo, protocatechuic acid and p-trans-coumaric acid) were found to have anti-clastogenic activity (protective effect against chromosomal aberrations). Since the anti-clastogenic irridoids had an alpha-unsaturated carbonyl group, this structure was considered to play an important role in the anti-clastogenicity (Nakamura, 1997).

Ingestion of EU bark and leaves, and/or their extracts, cause no known side effects.

In accordance with the present invention, the inventors have determined that certain extracts of EU exhibit steroidogenic activity. The identification of the activity in EU extracts permits the rational design of therapeutic protocols and compositions useful in ameliorating the symptoms of disease conditions. It also permits the production of the active agents in the extracts in purified or chemical synthetic form.

SUMMARY OF THE INVENTION

In the context of the present invention, a composition "consisting essentially of" recited ingredients will elicit physiological conditions and responses mediated by estrogen or estrogen receptor or androgens or androgen receptors, preferably in a synergistic manner compared to the response obtained using estrogen or androgen alone as the eliciting compound. As a preferred instance of synergistic effect, a basal degree of activity of steroid alone or of the composition alone might be two-fold activation of the steroid receptor activity. Synergistic action is observed when greater than four-fold activation is observed, preferably when greater than six-fold activation is observed, more preferably when greater than eight-fold activation is observed, even more preferably when greater than 10-fold activation is observed when the steroid and the composition of the invention are applied together in the assay.

One aspect of the present invention is a method of extracting active steroidogenic compounds from EU plants. The steps comprise macerating the tissues of the EU plant, extracting the active compounds with steroidogenic activities with a solvent system, separating the liquid from the solid phase and adding water to precipitate the undesired compounds that may cause side-effects and/or reduce efficacy of the main active compounds with steroidogenic activities. As tissues of the EU plant, all tissues can be used; bark or leaves are preferred, and bark is most preferred.

According to this invention, the term ethanolic EU extract refers to EU extract using a solvent system consisting only of ethanol. The term hydroethanolic EU extract refers to the EU extract using a solvent system comprising ethanol and 20% water, in which the water component could be added before or after the extraction process. For the purpose of the examples, the extract was dried, weighed and resuspended in ethanol at a known concentration.

Another aspect of the present invention contemplates a method of modulating a steroidogenic-mediated physiological condition in a subject, said method comprising administering to said subject an effective amount of a formulation comprising an extract of EU or botanical or horticultural equivalents of EU or chemical or functional equivalents of the extract or a purified, or chemically synthesized form of one or more components of the extract. Another aspect of the present invention is directed to a composition comprising a part of EU or a botanical or horticultural equivalent of EU or an extract thereof or chemical or functional equivalents of the extract or a purified, or chemical synthetic form of one or more components of the extract wherein said composition is effective in modulating a steroidogenic-mediated condition in a subject.

Another aspect of the invention is an article of manufacture that comprises an extract of the invention, or a purified or chemically synthesized molecule that is a component of the extract, that has steroidogenic activity, preferably synergistic activity together with a steroid compound (especially with an androgen or estrogen compound). In such an article of maufacture, the extract or purified or synthesized component is packaged together with written materials that provide instructions or describe or urge use of the extract or purified or synthesized component to modulate, and especially to enhance, a physiological condition or response mediated by a steroid, especially a condition or response mediated by an androgen receptor or by an estrogen receptor.

Yet another aspect of the present invention is directed to a purified or chemical synthetic molecule form of EU, or a botanical or horticultural equivalent thereof, or an extract thereof which molecule is capable of modulating a steroidogenic-mediated condition.

Still another aspect of the present invention provides for the use of EU or a botanical or horticultural equivalent thereof or an extract thereof or a chemical or functional equivalent of the extract or a purified or chemical synthetic form of one or more components of the extract in the manufacture of a medicament for the treatment of steroidogenic-mediated conditions.

Androgen-induced transactivation activity was used as a measure of androgenic activity and was measured with an androgen-regulated reporter gene, ARE-Tata-Luc, and expressed as fold increase in luciferase activity compared with cells not exposed to androgen. Each data point is the mean±(SE) of triplicate samples.

Figure 1A:
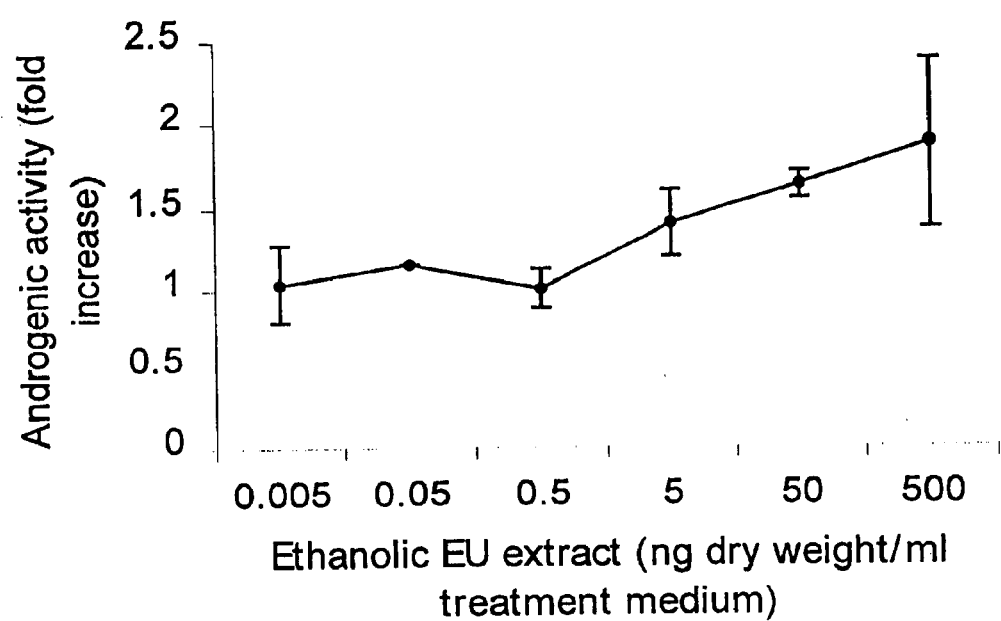
FIGS. 1A to 1E are graphical representations showing the dose-dependent responses of five treatments: (a) androgenic activity of an ethanolic EU extract; (b) androgenic activity of an hydroethanolic EU extract; (c) testosterone-potentiating activity of a fixed dose of ethanolic EU extract (50 ng dry weight/ml treatment medium) with increasing doses of testosterone; (d) DHT-potentiating activity of a fixed dose of ethanolic EU extract (50 ng dry weight/ml treatment medium) with increasing doses of DHT; (e) DHT-potentiating activity of increasing doses of the ethanolic EU extract with a fixed dose of DHT (1 nM).
Figure 1B:
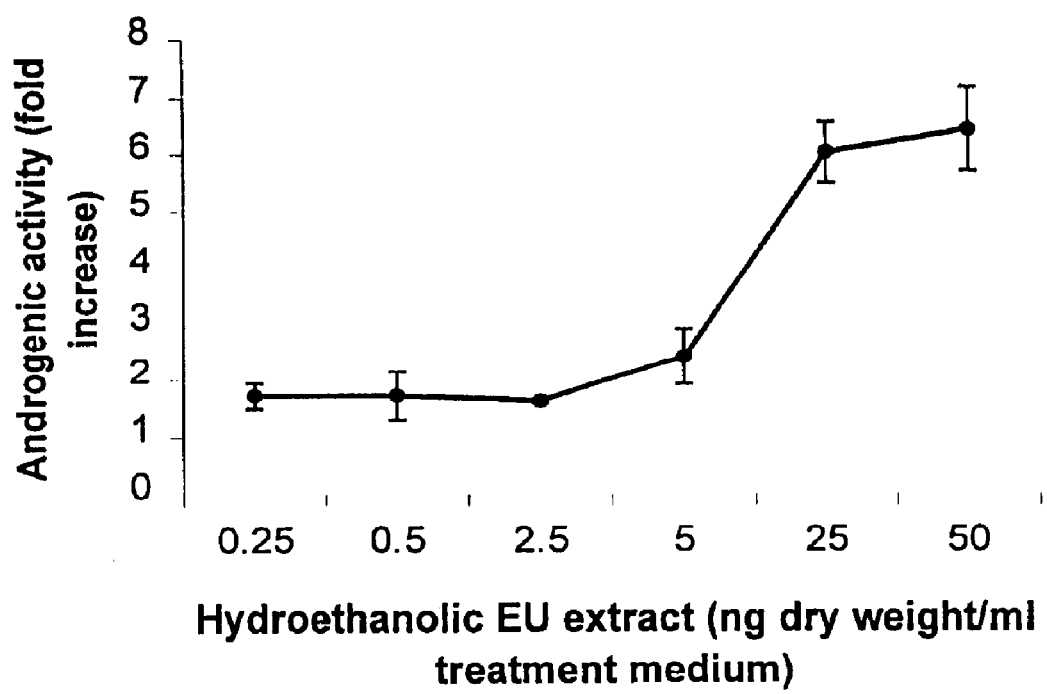

HeLa cells transiently expressing androgen receptor were exposed to increasing doses of ethanolic EU extract (FIG. 1a). Similarly, androgen receptor expressed in HeLa cells were also exposed to increasing doses of an ethanolic EU extract precipitated with 20% deionized water (hydroethanolic EU extract) (FIG. 1b). Treatments were also carried out using increasing doses of testosterone with an ethanolic EU extract at a fixed concentration of 50 ng/ml (FIG. 1c), increasing doses of DHT with an ethanolic EU extract at a fixed concentration of 50 ng/ml (FIG. 1d) and 1 nM DHT with different doses of an ethanolic EU extract (0 ng/ml to 50 ng/ml) (FIG. 1e).

Figure 2:
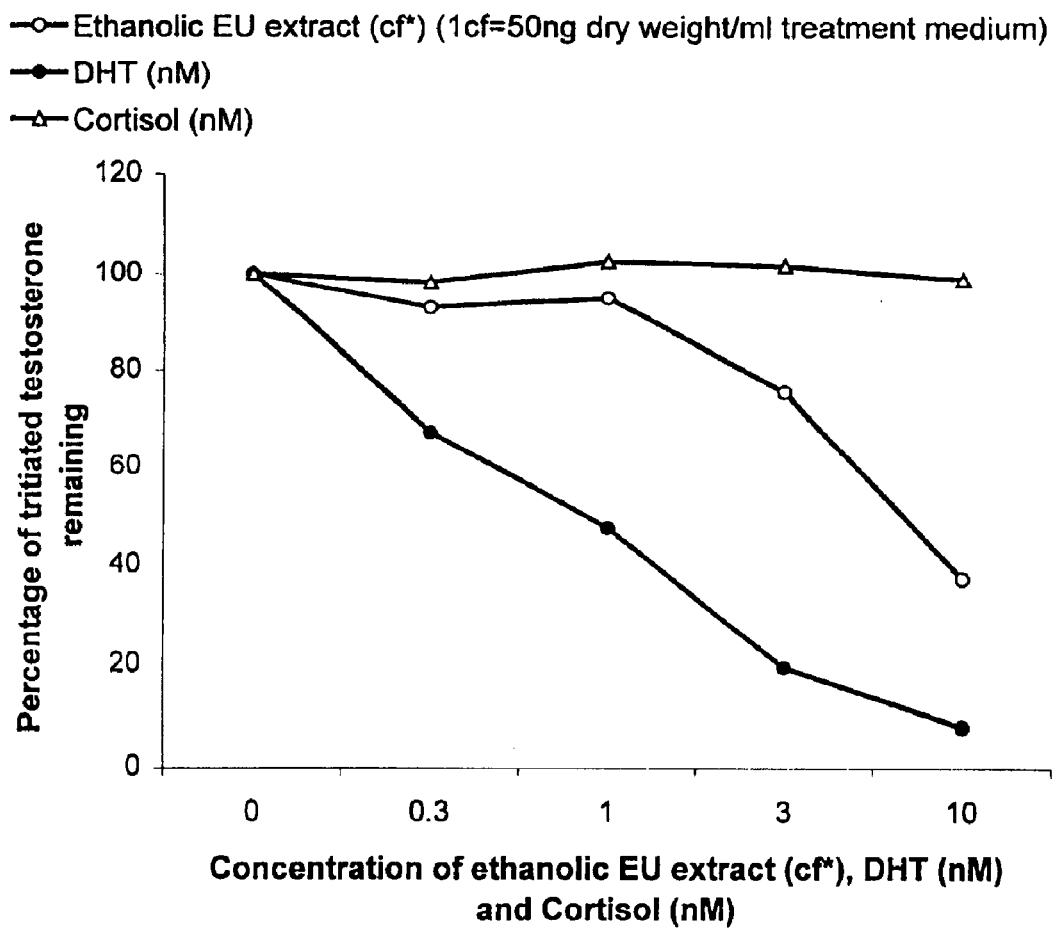

FIG. 2 is a graphical representation showing radioligand displacement assay of an ethanolic EU extract. COS-7 cells were transfected with DNA encoding AR and then exposed to 3 nM of tritiated testosterone and the indicated amounts of DHT (nM), cortisol (nM) or ethanolic EU extract (concentration 1=50 ng/ml) for 2 hours at 37° C. The treated cells were harvested and the amount of tritiated testosterone bound to AR is measured by scintillation counting. Specific binding is expressed as percent tritium bound to AR, where 100% is the amount of specific tritiated-testosterone bound in the absence of competing cold ligand minus background (non-specific binding to substrate and proteins). Each data point, the mean of quadruplicates, represents the amount of radiolabelled testosterone specifically bound on exposure to indicated doses of DHT, cortisol or ethanolic EU extract.

Figure 3:
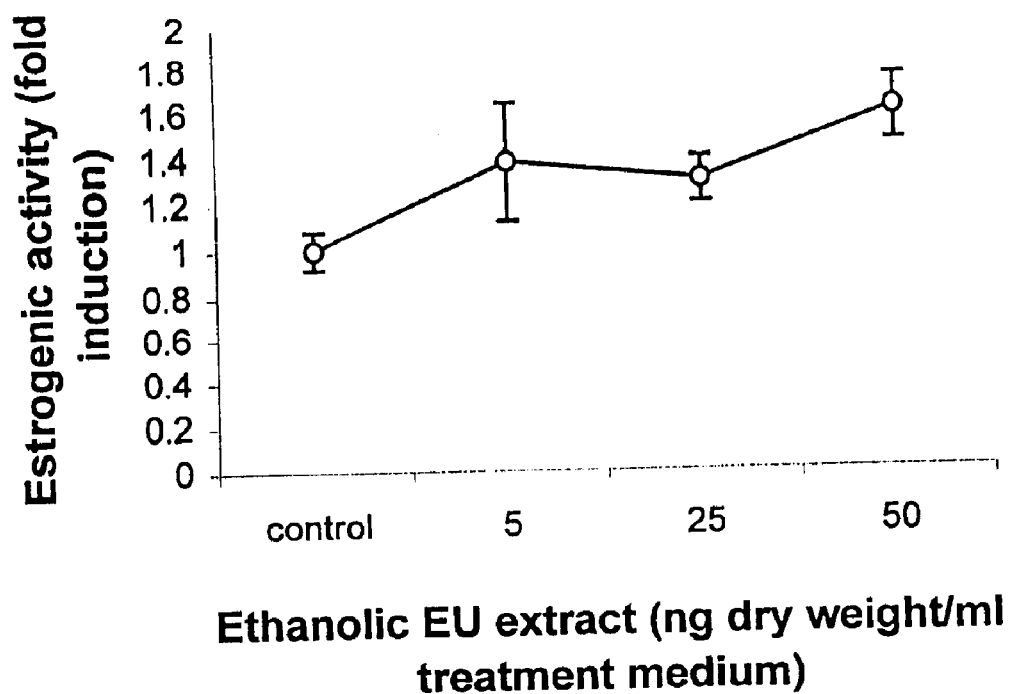

FIG. 3 is a graphical representation of estrogenic effect of EU. Hela cells were transfected with DNA encoding human estrogen receptor and the estrogenic effect of an ethanolic EU extract measured with MMTV-ERE-LUC reporter gene. Control cells were not exposed to the ethanolic EU extract while other cells were exposed to indicated doses of the ethanolic EU extract. Estrogenic activity is expressed as fold increase in reporter gene activity compared to control. Data are mean±SE of triplicate samples.

Figure 4:
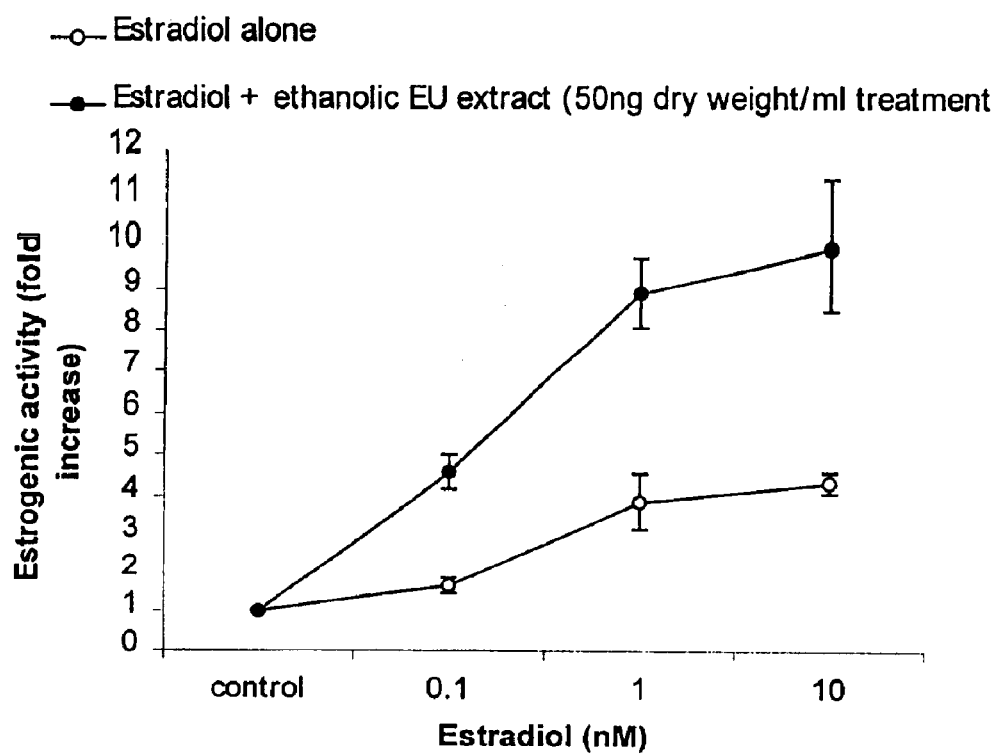

FIG. 4 is a graphical representation of the synergistic effect of an ethanolic EU extract on estradiol action. Hela cells were transfected with DNA encoding human estrogen receptor and the estrogenic effect was measured with a MMTV-ERE-LUC reporter gene. Cells were exposed to increasing doses of estradiol, with or without 50 ng/mL of the ethanolic EU extract, as indicated. Control cells were not exposed to the ethanolic EU extract or estradiol. Estrogenic activity is expressed as fold increase in reporter gene activity compared to control. Data are mean±SE of triplicate samples.

Figure 5:
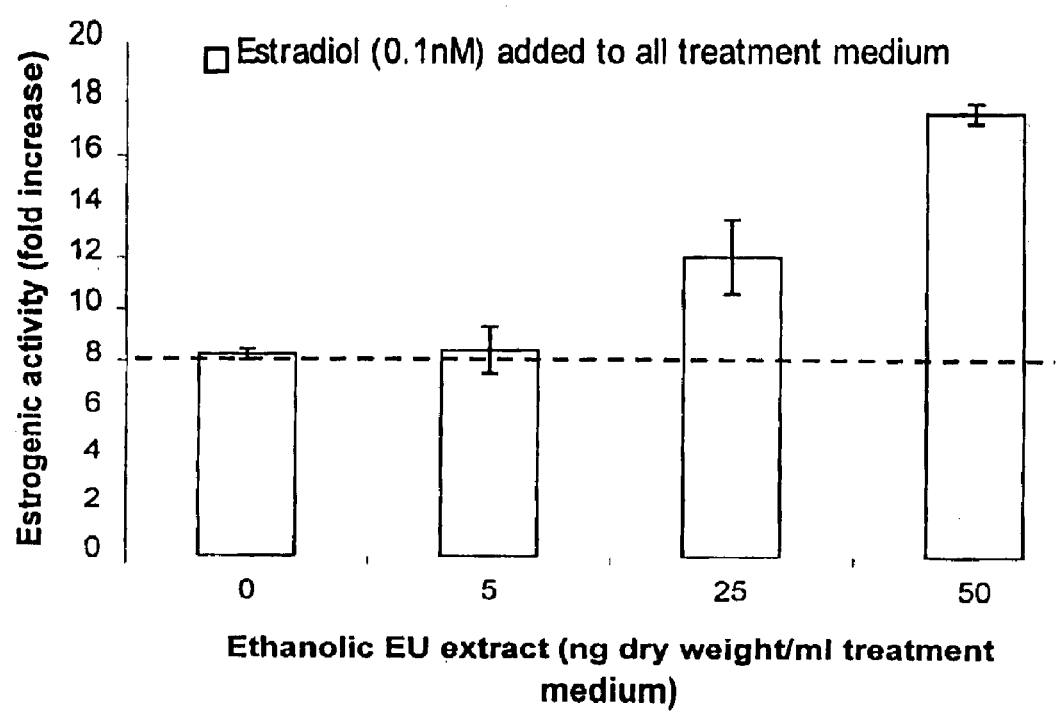

FIG. 5 is a graphical representation of the effect of increasing doses of an ethanolic EU extract on estradiol action. Hela cells were transfected with DNA encoding human estrogen receptor and the estrogenic effect was measured with a MMTV-ERE-LUC reporter gene. Cells were exposed to 0.1 nM estradiol and increasing doses of the ethanolic EU extract as indicated. Control cells were not exposed to the ethanolic EU extract. Estrogenic activity is expressed as fold increase in reporter gene activity compared to control. Data are mean±SE of triplicate samples.

Figure 6A:
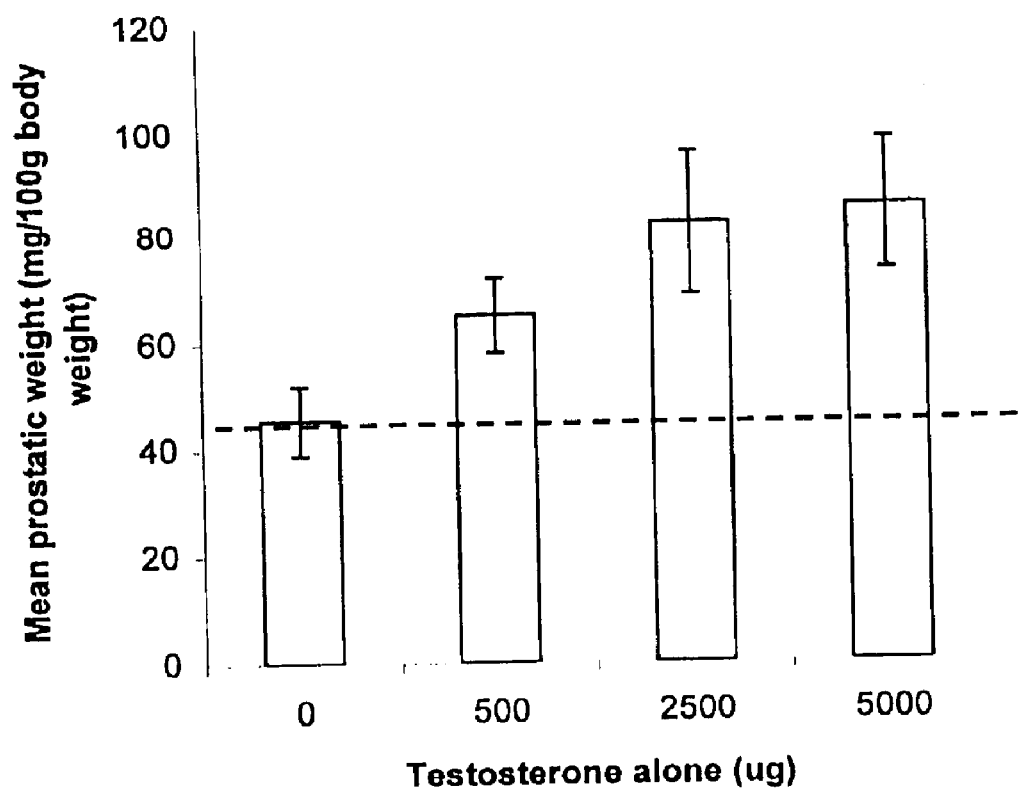
Figure 6B:
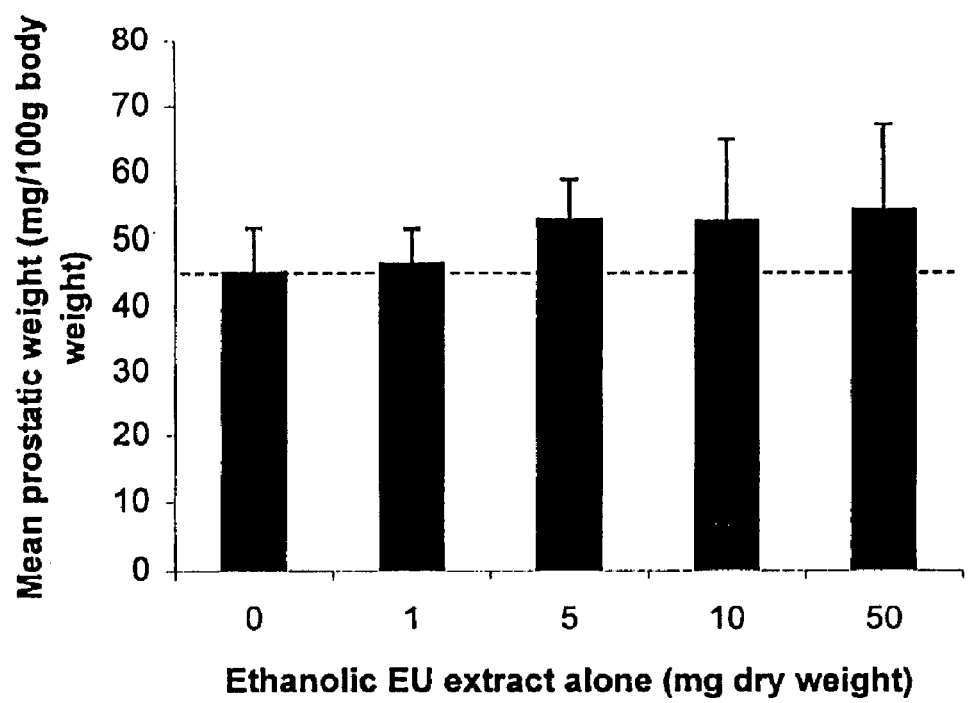
Figure 6C:
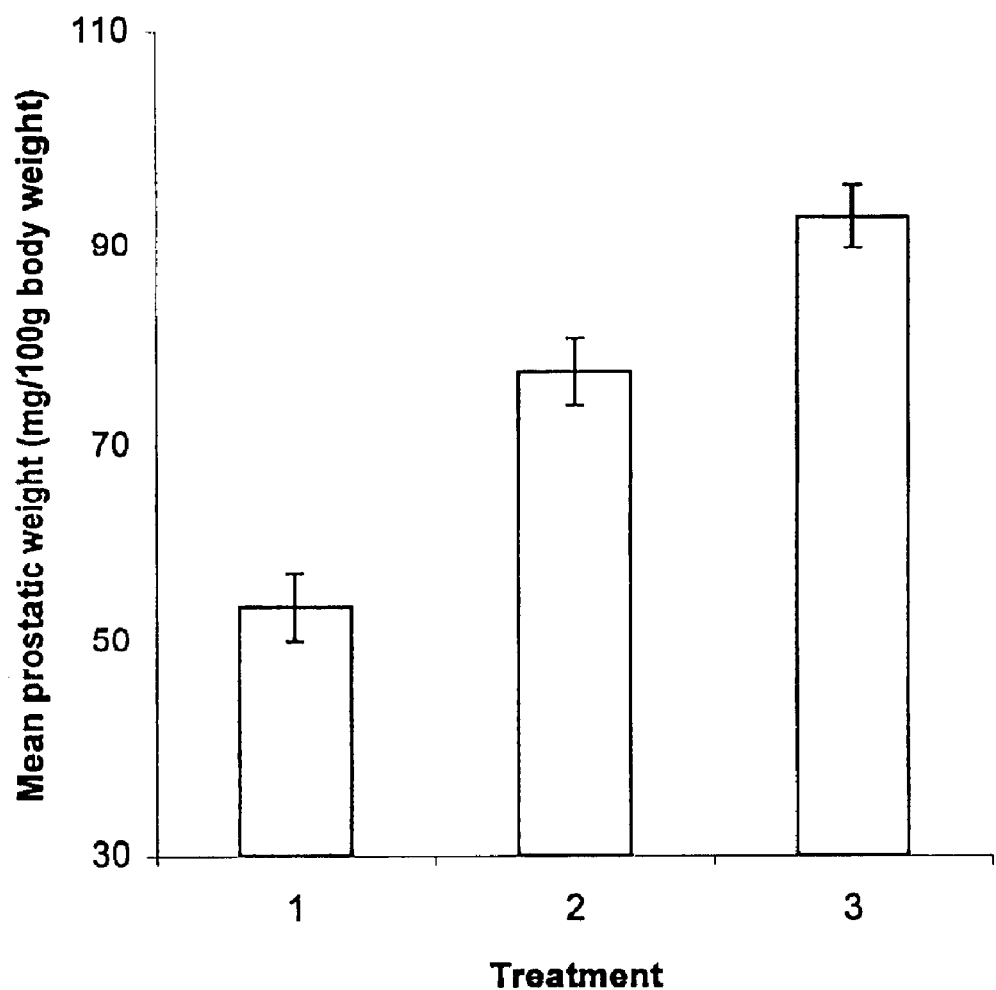

FIG. 6A to 6C is a graphical representation of androgenic studies in animal models demonstrating the synergistic effect of an ethanolic EU extract. The growth of the ventral prostate gland, an androgen-dependent tissue, in immature Wistar rats was measured. Administration of testosterone by intramuscular injection alone resulted in dose-dependent increments in prostatic weight (FIG. 6A). Oral dosing of the animals with the ethanolic EU extract alone, at doses from 1/mg to 10/mg, also resulted in dose-dependent increments in prostatic weight (FIG. 6B). Treatment of animals by intramuscular injection of a high dose of testosterone (5 ug) and also orally feeding 50/mg of the ethanolic EU extract indicated a highly significant synergistic effect whereby the ethanolic EU extract was able to increase prostatic growth to above that observed with the high dose of testosterone alone (FIG. 6C).

FIG. 7a is a graphical representation of the solid phase separation of androgenic activity of compounds in an ethanolic EU extract. A 50 ml Diol matrix was loaded into a glass column and an ethanolic EU extract (50 mls) was dry packed on top of the Diol matrix. The ethanolic EU extract was then sequentially eluted into individual fractions using 150 ml of each of the following solvents of increasing polarity in the following order: hexane 100%, hexane:dichloromethane (DCM) (1:1), DCM 100% and methanol (MeOH) 100%. The fractions were dried down in a rotary evaporator at 37° C. and resuspended in equivalent amounts of ethanol for assay of androgenic activity as in FIG. 1. All experiments were preformed in the presence of 1 nM of the synthetic androgen, miborelone (MB) and data are expressed with MB activity as 100%.

Figure 7B:
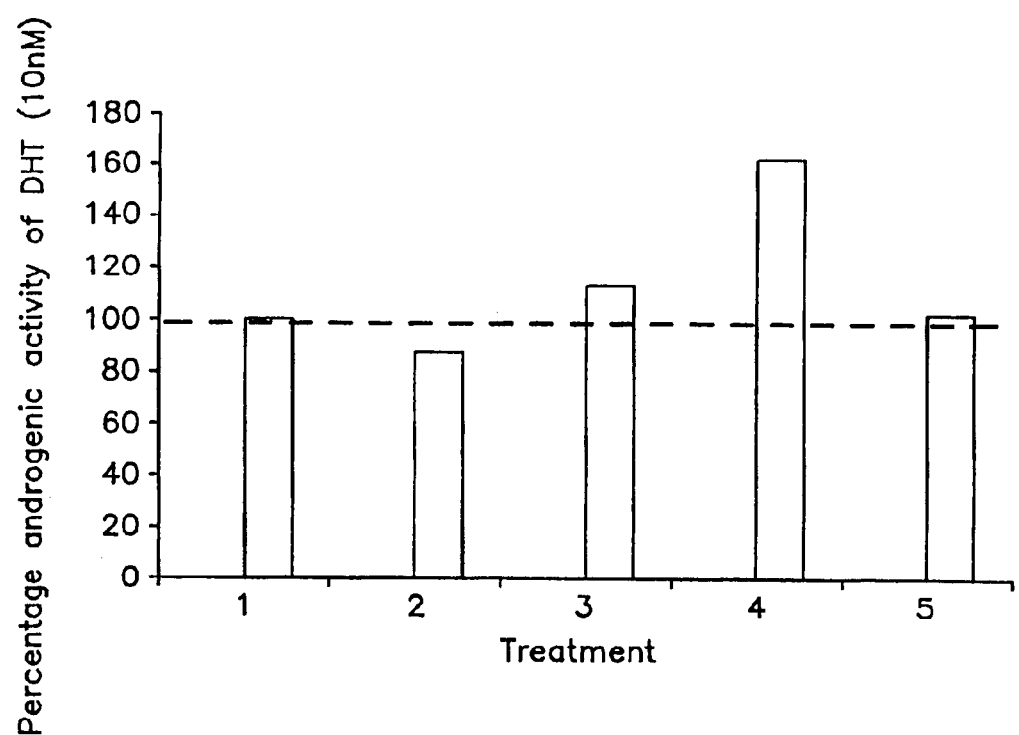

FIG. 7b is a graphical representation of the solid phase separation of androgenic activity of compounds in an ethanolic EU extract using more defined solvents. Experiments were conducted as in FIG. 7a except that the following solvents were used DCM, ethyl acetate and ethanol (EtOH). The column was eluted first with 150 ml of DCM, then followed by 150 ml of ethyl acetate and finally with 300 ml of EtOH. The EtOH eluate was individually collected into two separate, sequential fractions: EtOH I and EtOH II. All experiments were performed in the presence of 10 nM of the physiological androgen, dihydrotestosterone (DHT).

Figure 8A:
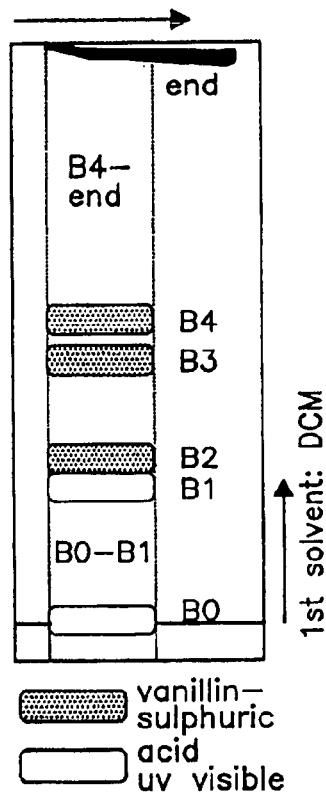
Figure 8B:
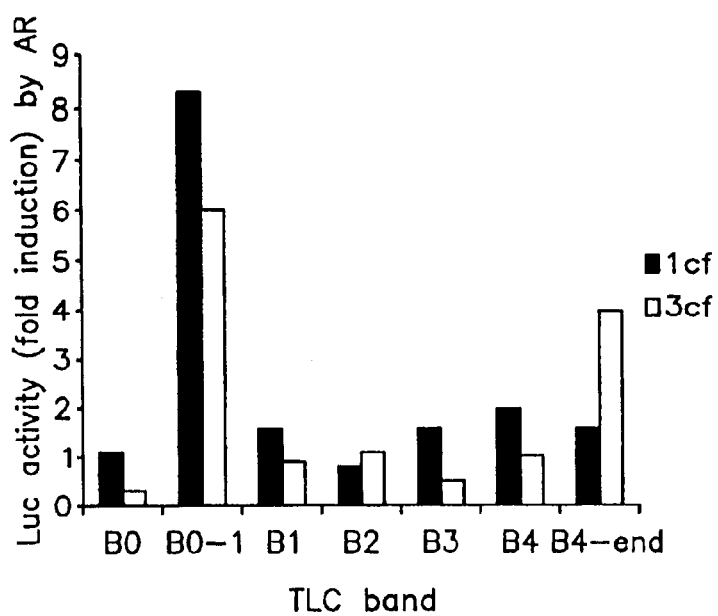

FIG. 8. Fractionation of an ethanolic EU extract with flash chromatography using Sephadex LH-20 followed by thin layer chromatography (TLC) silica gel 60 matrix in conjunction with bio-characterisation using AR gene expression. FIG. 8a shows that an n-butanolic fraction (F1) from a Sephadex LH-20 separation of the ethanolic EU extract was further resolved into distinct bands (B0, B0-1, B1, B2, B3, B4, B4-end) which can be visualized with either ultraviolet (UV) illumination or with a chemical reagent (vanillin-sulphuric acid). Upon bioassays with the AR, the agonistic activity of the ethanolic EU extract can be separated into phytocompounds with widely/differing hydrophilicity by TLC (FIG. 8b). TLC band B0-1 (more strongly-interacting with silica gel) can activate the AR in an agonistic manner as indicated in FIG. 8b, at relative concentrations of 1 concentration factor (cf) and 3 cf. Similarly, band B4-end also demonstrates agonistic bioactivity albeit only more markedly at a higher concentration of 3 cf.

Figure 9:
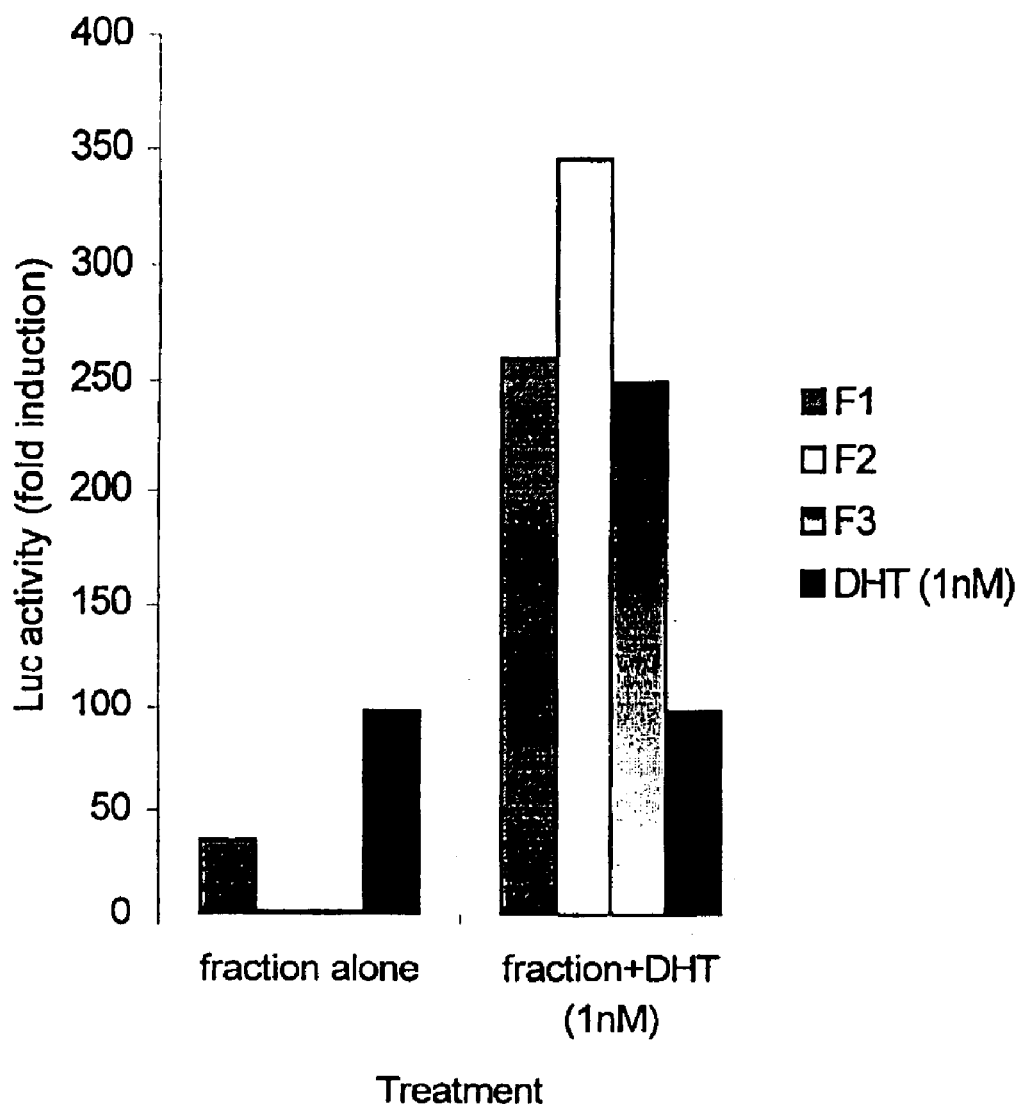

FIG. 9. Fractionation and bioactivity characterisation of an ethanolic EU extract with high performance liquid chromatography (HPLC) using a reverse phase C-18 semi-preparative column in conjunction with downstream AR bioassays. The HPLC column was eluted with an acetonitrile gradient mobile phase. (A chromatogram is shown as FIG. 10.) F1 is the fraction that elutes between 40 min to 60 min time interval. F2 is the fraction eluting between 60 min to 80 min while F3 shows bioactivity of fraction eluting between 80 min to 120 min. The Figure shows biological activity of the fractions. The black bar indicates AR activity in the presence of the androgen dihydrotestosterone (DHT). F1 demonstrates both androgen-like (agonist) activity on its own (fraction alone) and also androgen-boosting activity in the presence of DHT (fraction+DHT). In contrast, F2 and F3 show only minimal agonist activity (fraction alone) but demonstrate strong androgen-boosting activity in the presence of DHT (fraction+DHT).

Figure 10:
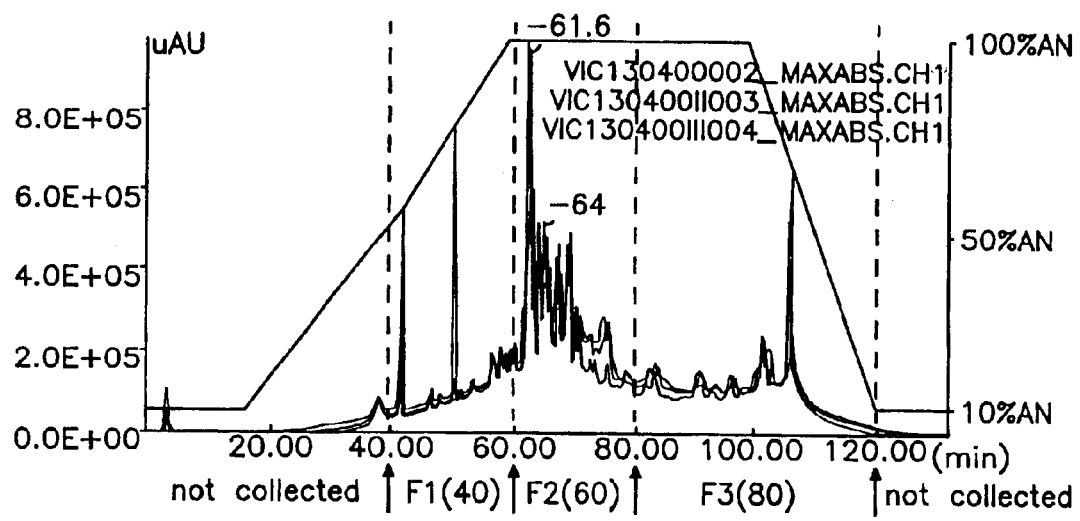

FIG. 10. HPLC Chromatogram. Elution profiles of three runs of the reverse-phase HPLC chromatography performed as in Example 9 are superimposed. Fractions F1, F2 and F3 are indicated between vertical arrows. The acetonitrile gradient is shown v. time.

DETAILED DESCRIPTION OF THE PREFERRED EMBODIMENTS

The present invention is predicated in part on the identification of steroidogenic-modulating properties in a formulation comprising parts of EU or an extract thereof.

Accordingly, one aspect of the present invention is a method of extracting active steroidogenic compounds from EU plants. EU plant parts are macerated prior to the actual extraction process. Fresh EU plant parts or preferably dried plant parts are macerated using any of the known process such as chopping into small pieces, grinding into powder or breaking up into fine particles using a high speed blender. Although active compounds with steroidogenic activities can be extracted from different parts of the EU plant, the preferred part of the EU plant for extraction is the bark.

A soaking method is one of the several methods of extracting the active compounds from the EU plant. In this method, the macerated plant is soaked with a solvent system and left for a period of time to allow the active compounds to dissolve into the solvent system. To enhance the diffusion of the active compounds into the solvent system, the mixture can be mechanically agitated and/or heated to a pre-determined temperature. The mechanical agitation methods include but are not limited to the following: shaking, vortexing, swirling, stirring and ultrasonicating.

After a sufficient period of time for the diffusion of the active compounds into the solvent system, the liquid is separated from the solid by any one of the well-known techniques such as filtration and centrifugation.

The solvent system can comprise any of the well-known systems such as an organic solvent or a combination of organic solvents. Preferably, the organic solvent is alcohol and more preferably, ethanol. Other organic solvents such as hexane, dichloromethane, ethyl acetate will also be effective. Water can be part of the solvent system. The percentage of water can range from 0% to 100%. If water is not part of the initial solvent system, water can be added to the liquid phase during any part of the soaking period. It is also possible to add water to the liquid phase after separation from the solid phase. One of the effects of the addition of water is to cause precipitation of non-steroidogenic compounds that may have adverse side-effects. Water can be added up to 20% by volume.

Another method of extracting active compounds from the macerated EU plant is to percolate the macerated EU plant with a continuously refluxed solvent system such as the soxlet-type method for extraction. After completion of the extraction process, the liquid containing the active compounds may be mixed with water (up to 20% by volume) to precipitate the undesired compounds. The precipitate can be separated from the liquid containing the active compounds with steroidogenic activity using any one of the well known separation methods such as filtration and/or centrifugation.

The solvents in the liquid phase containing the active compounds with steroidogenic effects can be evaporated off using any of the well known drying methods including but not limited to, rotary evaporation, speed-vacuum centrifugation or open-top drying. The dried extract is then suitable for use or storage. If desirable, the dried extract can be resuspended in suitable solvents prior to use.

For further purification, the extract, either dried and then redissolved in an appropriate solvent, preferably water or an alcohol, can be applied to a reverse phase chromatography column and the steroidogenic compounds can be eluted with a mobile phase comprising water and acetonitrile. Alternatively, or in combination with the reverse phase purification, the extract can be applied to a chromatography matrix comprising dextran crosslinked by an alkyl ether and the steroidogenic compounds can be eluted with an alcohol, preferably a $C_1$–$C_6$ alkyl alcohol, more preferably an n-alkyl alcohol.

Accordingly, another aspect of the present invention contemplates a method of modulating a steroid-mediated physiological condition in a subject, said method comprising administering to said subject an effective amount of a formulation comprising an extract of EU or botanical or horticultural equivalents of EU or chemical or functional equivalents of the extract or a purified or chemical synthetic form of one or more components of the extract.

A "steroid-mediated physiological condition" includes an androgen-mediated physiological condition, an estrogenic-mediated physiological condition and/or other physiological condition mediated through the steroid/nuclear receptor family of proteins. A "steroidogenic agent" includes an androgen, an estrogen and/or any other ligand interacting with the steroid/nuclear receptor family of proteins. Estrogenic agents are useful in hormonal therapy in hypoestrogenic states such as but not limited to menopause, osteoporosis and cardiovascular disease. An "estrogen-mediated physiological condition" also includes and encompasses conditions mediated via an estrogenic receptor or active or complex forms thereof.

Reference herein to an "androgen-mediated physiological condition" includes reference to the induction of physiological processes mediated via the androgenic receptor. These physiological processes include biological, endocrinological and other bodily processes which are induced, stimulated, enhanced or otherwise facilitated by the androgen receptor or androgen receptor complexes and/or its activated forms which are responsive to natural or synthetic androgens or other compounds which have androgenic properties such as being able to activate the androgen receptor.

The ability to activate or otherwise modulate the androgen and/or estrogen receptor may be tested in vitro or in vivo. Reference to in vivo includes the practice of the present invention in humans, primates, livestock animals (e.g. sheep, cows, pigs, goats, horses, donkeys), laboratory test animals (e.g. rabbits, mice, rats, guinea pigs), companion animals (e.g. dogs, cats) and captive wild animals.

For convenience, a "steroid receptor" encompasses the androgen receptor and/or estrogen receptor and/or other receptor belonging to the steroid/nuclear receptor family of proteins. A "steroidogen" encompasses an androgen, an estrogen and/or any other ligand interacting with the steroid/nuclear receptor family of proteins.

The term "modulate" and its variations including "modulating" and "modulates" includes the up-regulation and down-regulation of steroidogenic receptor activity or the activity of steroidogen-steroidogen receptor complex activity. This may be conveniently determined at the level of up-regulating or down-regulating target gene expression following modulation of steroidogen receptor activity.

The present invention is particularly directed to a formulation comprising EU or parts thereof or an extract thereof or botanical or horticultural equivalents of EU or chemical or functional equivalents of the extract from EU extract or purified or chemical synthetic forms of one or more components in EU or an extract thereof.

Reference herein to "*Eucommia Ulmoides*" or "*E. Ulmoides*", or "Du Zhong", or "EU" includes reference to botanical and horticultural equivalents thereof. Botanical and horticultural equivalents includes herbs and other plants related at the genetic, biochemical, or medicinal level to EU. For example, a medicinally functional equivalent plant may be indigenous to another country. Such a plant is encompassed by the present invention. Botanical equivalents of EU are described by Gu et al. (Z. M. Gu et al., *Chung Kuo Chung Yao Tsa Chih* 14:714–7171 (1989)) and encompass plants that are used among different ethnic groups as substitutes for cortex eucommiae. Their study and identification of samples of all original plants and materia medica from all locations producing Du Zhong identified 48 species of ethnic substitutes for Du Zhong from 17 genera of 10' families:

1. Lauraceae Litsea 1 species
2. Anacardiaceae Rhus 1 species
3. Rosaceae Potentilla 1 species
4. Actinidiaceae Saurauja 1 species
5. Malvaceae Urena 1 species 6. Bignoniaceae Catalpa 1 species
7. Apocynaceae
   (1) Aistonia 1 species
   (2) Pararneria 1 species
   (3) Beaumontia 1 species
   (4) Chonemorpha 2 species
   (5) Trachelospermum 1 species
   (6) Ichnocarpus 1 species
   (7) Parabarium 4 species
8. Asclepiadaceae
   (1) Gymnema 2 species
   (2) Marsdenia 1 species
9. Araliaceae Hedera 1 species
10. Celastraceae Euonyrnus 27 species Horticultural equivalents of of EU include callus, meristem or tissues or cells maintained in in vitro culture.

Reference to the Du Zhong herb also encompasses natural and artificially created variants of EU. An artificially created variant includes a variant made by selective breeding or by genetic manipulation. A part of EU includes the bark, leaf, stem, root, flower, seed or other reproductive or vegetative portion of the plant or a combination of two or more of these portions.

The term "formulation" includes an extract of EU or parts thereof in liquid, solid or aerosol or vapour form. In a preferred embodiment, the formulation comprises an ethanolic or aqueous extract of EU.

Herbal extraction techniques were designed to maintain maximal levels of active components. The steps comprise macerating the preferred bark of the EU plant, extracting the active compounds with steroidogenic activities with a solvent system, separating the liquid from the solid phase and optionally adding water of up to 20% v/v to precipitate the undesired compounds that may cause side-effects and/or reduce efficacy of the main active compounds with steroidogenic activities. The solvent system is preferably an $C_1$–$C_6$ alcohol, which can also include water in an amount up to 20% v/v. The separation of the solvent extract from insoluble solids can be performed by any method typical in the art. Filtration is preferred, but centrifugation can also be efficiently employed.

The term "ethanolic EU extract" as used herein refers to EU extract using a solvent system consisting only of ethanol. A "hydroethanolic EU extract" refers to the EU extract using a solvent system comprising ethanol and 20% water, in which the water component could be added before or after the extraction process.

As defined herein, the EU extract is considered to exhibit steroidogen activity. More particularly, the extract itself or one or more components therein are considered herein to be "androgen modulators" or "estrogen modulators" (i.e. steroidogen modulators) in that the extract or its components are capable of modulating the activity of the androgen receptor or a complex comprising same and/or the activity of the estrogen receptor or a complex, etc. The steroidogen modulators of the present invention are isolatable or obtainable from EU are defined as being "phyto-androgens" or "phyto-estrogens" (i.e. phyto-steroidogens) due to their botanical origin. Reference to an "androgen" in the term "phyto-androgen" is not to imply any limitation as to the structure of the phyto-androgen and the term extends to any component of EU or any extract of EU or any component or extract from a botanical or horticultural relative of EU which is capable of modulating androgen-receptor activity. Androgen receptor activity is conveniently measured in vitro or in cell culture by assays of transactivation and/or downstream target gene expression. "Downstream target genes" whose expression is regulated by androgen receptor activation are known in the art. Transactivation assays, in which androgen or other steroid receptor binding sites are coupled to reporter genes and then these constructs are placed into cells either in vitro or in vivo, are well-known in the art. Androgen receptor activity can also be assessed in vivo by measurement of physiological or anatomical parameters, e.g. development of male sexual organs, increase in muscle mass or spermatogenesis, known in the art to be regulated by androgen activity. Accordingly, the term "androgen modulator" includes a formulation or composition or extract of EU or a part of EU or a purified or chemical synthetic form of a component of the extract or part of EU or its botanical or horticultural equivalent. Similar comments, in relation to development of feminine characteristics, including regulation of serum levels of hormones related to the estrus cycle, apply in relation to "phyto-estrogen".

Reference herein to the "androgen receptor" or "estrogen receptor" includes reference to the naturally occurring receptor or its recombinant forms as well as splice variants or other genetic variants including polymorphic variants. Furthermore, the term encompasses complexes comprising the receptor and other molecules (e.g. androgen or estrogen) as well as the receptor's monomeric, dimeric, trimeric or multimeric forms including homodimeric, homotrimeric, homomultimeric, heterodimeric, heterotrimer and heteromultimeric forms. The receptor may be membrane associated or it may have translocated to the nucleus or be associated with chromosomal DNA.

The androgen receptor when activated by androgens, including phyto-androgens, has the intrinsic ability to bind to specific DNA sequences. Following binding, the transcriptional activity of a target gene (i.e. a gene associated with the specific DNA sequence) is modulated as a function of the ligand bound to the receptor. Functional activity of androgen receptors can be measured with reporter gene(s), such as firefly luciferase, coupled to steroid response elements, that are co-expressed with the androgen receptor (Quigley, 1995).

Processes capable of being modulated by an androgen or via an androgen receptor, in accordance with the present invention, include but are not limited to, the in vivo modulation of male sexual development in the fetus, secondary sexual development at puberty and anabolic processes (muscle growth, bone density), male sex drive (libido), skin condition, hair growth and physical stamina in adults, lipid metabolism, modulation of androgen-related processes (e.g. aging, stamina, muscle tone, spermatogenesis and the like). As readily recognized by those of skill in the art, the availability of selective phyto-androgen(s) in EU extracts for the androgen receptor makes it possible, for the first time, to develop nutraceutics in the form of, for example, food supplements and natural medicines for human and animal consumption without the need for special prescriptions. Such in vivo applications of the invention process may allow the daily modulation of various biological processes related to androgen action with reduced occurrence of undesirable side effects and the like. Processes capable of being modulated by estrogen or via an estrogen receptor include menopause, osteoporosis and cardiovascular disease.

The ability of compounds of the invention to modulate such processes may be evidenced in any number of ways. For example, EU extracts, in the presence of a ligand (e.g. DHT) exert a potentiating effect on the expression of genes under the control of androgen-response elements.

Accordingly, another aspect of the present invention is directed to a composition comprising a part of EU or a botanical or horticultural equivalent of EU or an extract thereof or chemical or functional equivalents of the extract or a purified or chemical synthetic form of one or more components of the extract wherein said composition is effective in modulating a steroidogenic-mediated condition in a subject.

The composition of the present invention may also be referred to as a herbal composition, natural medicine, a formulation and/or a formulation or composition with medicinal or ameliorating properties. The terms "formulation" and "composition" are used herein interchangeably.

The subject formulation in the form of a part of EU or an extract thereof may be administered in any suitable form including ingestion, topical application or via vapour or aerosol means. The term "ingestion" includes administering the herb or extract via edible or liquid means.

For in vivo applications, the extract or plant parts can be incorporated into a pharmaceutically acceptable formulation including a carrier or diluent for administration. Those skilled in the art will readily determine suitable dosage levels.

Reference herein to "suitable dosage levels" includes reference to levels of phyto-steroidogens sufficient to provide circulating concentrations high enough to effect activation of steroidogen receptor(s) or to agonize activity of a steroidogen-steroidogen receptor complex. Such a concentration typically falls in the range of about 1 nM up to 2 nM; with concentrations in the range of about 100 nM to 200 nM being preferred. Generally, however, the concentration is measured in terms of w/w of dried extract or v/v of liquid extract.

Exemplary mass amounts are from 1 to about 80% w/w or more particularly from 5 to about 50% w/w or even more preferably from 5 to about 20% w/w.

Exemplary pharmaceutically acceptable carriers include carriers suitable for oral, intravenous, subcutaneous, intramuscular, subcutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups and the like, optionally containing additives such as wetting agents, emulsifying and suspending agents, sweetening, flavouring and perfuming agents, and the like.

For the preparation of fluids for parenteral administration, suitable carriers include sterile aqueous or non-aqueous solutions, suspensions or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain additional ingredients such as preserving, wetting, emulsifying and dispersing agents. Formulations may be sterilized, for example, by filtration through a bacteria-retaining filter, by incorporating sterilizing agents into the compositions, by irradiating the compositions, or by heating the compositions. They can also be manufactured as solutions in sterile water, or some other sterile injectable medium, immediately before use.

The present invention further contemplates purified or chemical forms of one or more components of EU or its extracts. A "purified" form means a component which has undergone at least one purification step such as HPLC, electrophoresis, immunoprecipitation, ammonium sulphate precipitation or high speed centrifugation.

Accordingly, another aspect of the present invention provides a purified or chemical synthetic molecule form of EU or a botanical or horticultural equivalent thereof or an extract thereof which molecule is capable of modulating an steroidogenic-mediated condition.

Purification of components in the EU extract may be readily accomplished by any convenient means. For example, the extract may be fractionated and fractions then tested in a cotransfection bioassay (e.g. see Ong, 1999). In this assay, an EU extract or a fraction thereof is contacted with a cell cotransfected with a steroidogen receptor expression plasmid and a luciferase-receptor plasmid containing two steroidogen responsive elements. Luciferase activity is then a measure of steroidogenic activity. Any other reporter molecule may be used.

Accordingly, another aspect of the present invention contemplates a method for identifying a component of EU having steroidogenic properties, said method comprising contacting an extract of EU or a fraction of said extract with cells cotransfected with a steroidogen expression plasmid and a genetic sequence encoding a reporter molecule containing an steroidogen responsive element and determining the level of activity of the receptor molecule.

Yet another aspect of the present invention is directed to the use of EU or a botanical or horticultural equivalent thereof or an extract thereof or a chemical or functional equivalent of the extract or a purified or chemical synthetic form of one or more components of the extract in the manufacture of a medicament for the treatment of steroidogenic-mediated conditions.

Still yet another aspect of the present invention provides a method for hormonal therapy in a subject, said method comprising administering to said subject an effective amount of an extract of EU or botanical or horticultural equivalents of EU or chemical or functional equivalents of the extract or a purified or chemical synthetic form of one or more components of the extract for a time and under conditions to modulate steroidogenic activity.

In one embodiment, the steroidogenic activity is androgenic activity. This is important for modulating male sexual development, sexual function and infertility amongst other conditions.

In another embodiment, the steroidogenic activity is estrogen activity. The latter is important for the treatment of menopause, osteoporosis and cardiovascular disease amongst other conditions.

The present invention is further described by the following non-limiting Examples.

EXAMPLE 1

Extraction and Formulation

One kg of bark of the EU plant, or other plants as described in Example 2 below, was ground into powder with a grinding machine. The ground plant bark was placed in a vessel and the active compounds with steroidogenic activities were extracted with 10 liters of 100% ethanol by soaking the ground bark for 1 week, to allow the active compounds to dissolve into the solvent system. The liquid phase was then separated from the solid phase by filtration with a Whatman-1 filter paper. Samples prepared in this manner are hereinafter referred to as "ethanolic extracts".

In some instances, a portion of the ethanolic extract was then further purified by addition of distilled water to 20% v/v. Material that precipitates as a result was removed by filtration with Whatman-1 filter paper. The resulting liquid fractions are hereinafter referred to as "hydroethanolic extracts".

EXAMPLE 2

Identification of Herbal Extracts which Activate Androgen Receptor

As part of an ongoing bioprospective search for ethanobotanical herbs which contain novel phyto-androgens that act through the androgen receptor, a multitude of extracts, prepared as in Example 1 from medicinal herbs identified by pharmacognosy, were screened utilizing a cotransfection bioassay similar to that described by Ong, 1999

Candidate herbal extracts were initially tested in HeLa cells cotransfected with an androgen receptor expression plasmid and a luciferase-receptor plasmid containing two androgen responsive elements (ARE). In this assay the androgenic activity of any added compound can be accurately measured.

Thus, HeLa cells were cotransfected with an androgen receptor (AR) expression plasmid, a plasmid for expression of β-galactosidase (β-gal) and a luciferase reporter plasmid, ARE-Tata-luc (Jenster 1997) and then incubated with ethanol as a solvent control, or with the herbal extracts indicated in Table 1. Herbal extracts were added to the cells six hours after transfection. Thirty-six hours later, the cells were harvested and cell extracts assayed for luciferase activity.

The AR expression and reporter gene vectors were transfected into HeLa cells, a human cell line exhibiting minimal endogenous AR expression, using the lipofection technique. The DNA mix contained an AR expression vector, a reporter gene vector (ARE-Tata-Luc) and a βGal vectors, the last for purposes of normalizing results for the transfection efficiency. The AR expression vector comprises a cDNA encoding AR and expressed from a SV40 promoter and a rabbit β-globin polyadenylation signal, all cloned in a pBR328 vector. The β-gal vector comprises a bacterial lacZ gene under control of an SV40 promoter-enhancer. The DNA mix was preincubated for 45 min at room temperature with lipofectamine (Promega, Madison, Wis.) in a 400 µl serum-free medium. The DNA-liposome complexes (total volume of 200 µl) were overlaid onto 50–60% confluent HeLa cells growing in 24 well plate. Transfection was continued for 5 hours before removal of the transfection mix and the replacement with growth medium containing 10% charcoal-stripped fetal calf serum, and indicated amounts of androgens and/or extract. After 40 to 48 h of incubation, the cells were rinsed twice with PBS, and lysed with 400 µl of reporter lysis buffer (Promega). Cells were scraped from the wells and after one freeze thaw cycle, the cell lysate was cleared by centrifugation at 12,000×g for 10 min. Cell lysates (100 µl) were added to 20 µl of luciferase substrate and luciferase activity measured with a luminometer. Transfection efficiency was assessed by βGal activity and luciferase activity normalized to the protein content of the cell lysates. Total protein in the supernatant was quantified with bovine serum albumin as the standard.

Table 1a shows that an ethanolic EU extract displayed significant androgenic activity increasing reporter gene activity, 41-fold (7.8% of the activity observed with 1 nM DHT), compared to controls not exposed to DHT or herbal extract. In contrast, two species of ginseng, *Panax quinquefolius* and *Panax ginseng* did not induce significant androgen receptor activity, giving only of 1.7-fold (0.3% of 1 nM DHT) and 1.9-fold (0.4% of 1 nM DHT) increases respectively. Similarly, Jamu Tongkat Ali (A Malayan aphrodisiac herbal composition comprising of *Engenia aromatica, Trigonella graecum, Zingiber officinale, piper nigrum, Cinnamomum sarivum, Amomum kepulaga, Cinnamomum zeylanicum, Eurycoma longifolioa*) demonstrated little androgenic activity with an induction value of only 1.2-fold (0.2% of 1 nM DHT).

Table 1b shows that only an ethanolic EU extract was able to potentiate androgen activity, by increasing DHT activity to 187% of that observed with DHT alone. In comparison, none of the other herbal extracts,—SB (*Evodia rutaecarpa*), SE (*Syzygium aromaticum*), SY (*aconitum carmichaeli*), SZ (*Alpinia oxyphylla*) were able to potentiate the effect of DHT on the AR.

Table 1c shows that an ethanolic EU extract did not activate the closely related progesterone and glucocorticoid receptors, showing only 1.3 and 2.2-fold activity, respectively, compared to 41-fold activity observed with the androgen receptor above (Table 1a). Similarly, in the presence of their respective ligands, an ethanolic EU extract did not potentiate PR and GR activity. The presence of an ethanolic EU extract and cognate ligands induced only 64 and 99% of the activity observed with the cognate ligands alone, when tested with the progesterone and glucocorticoid receptors, respectively. Thus, the stimulatory activity of an ethanolic EU extract on the androgen receptor was not observed with the glucocorticoid or progesterone receptors.

EXAMPLE 3

Transactivation Studies

To further characterize the androgenic activity of the EU, the extract alone (either ethanolic EU extract or hydroethanolic EU extract as indicated accordingly), and in combination with testosterone and DHT, were tested for their transactivation properties.

FIG. 1 shows the dose-dependent responses of the five different treatments:

FIG. 1a—different concentrations of an ethanolic EU extract

FIG. 1b—different concentrations of a hydroethanolic EU extract (after 20% water precipitation of insoluble compounds).

Figure 1C:
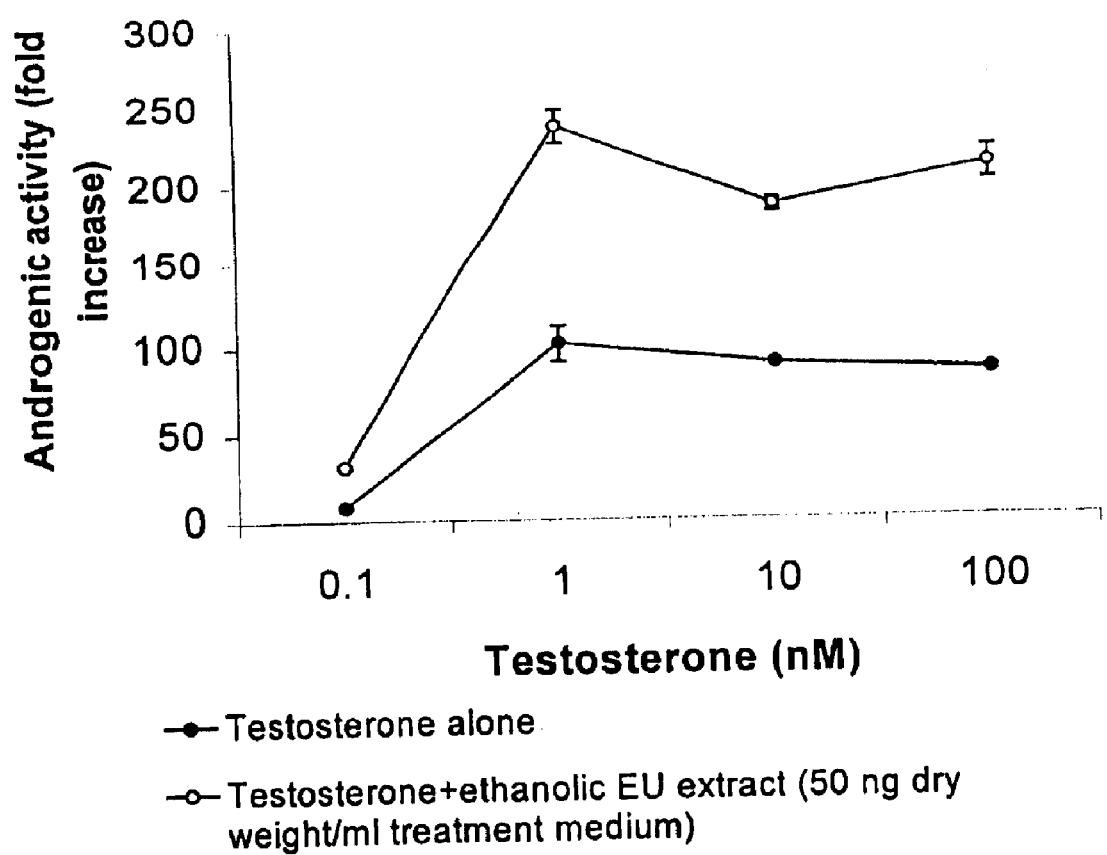
Figure 1D:
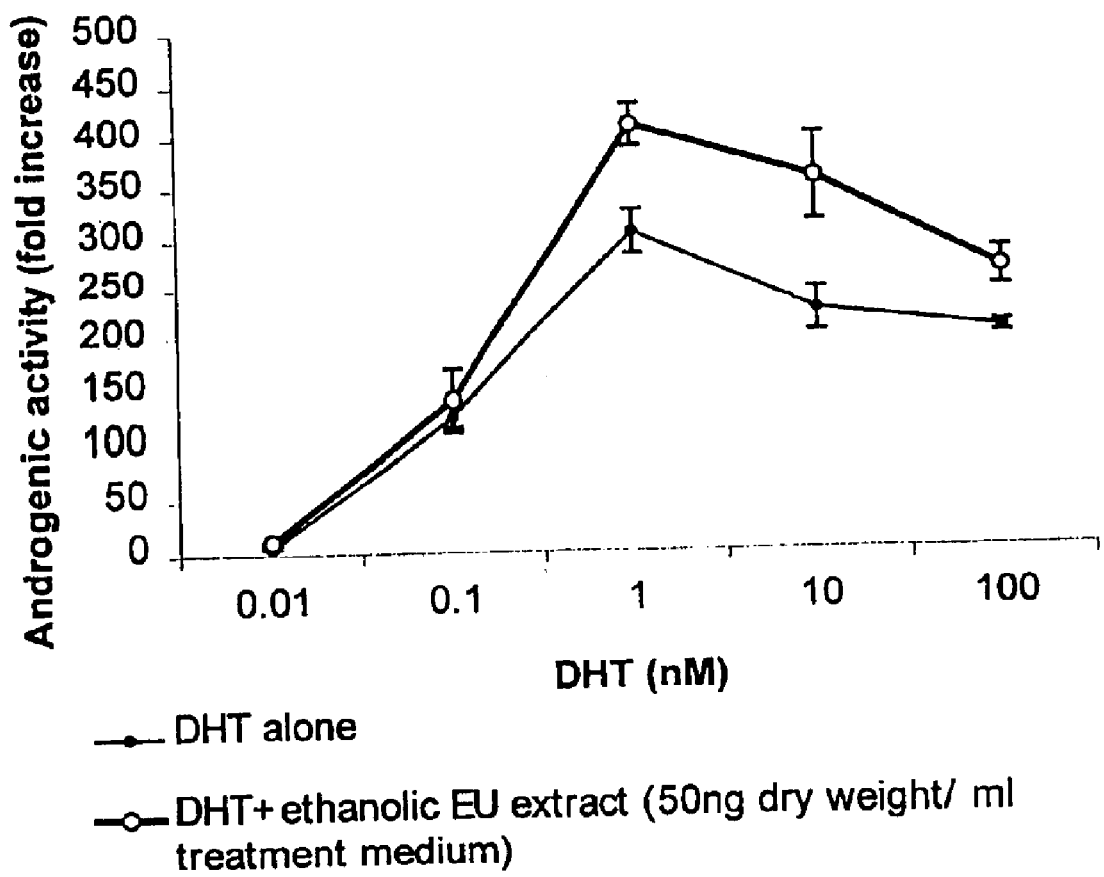
Figure 1E:
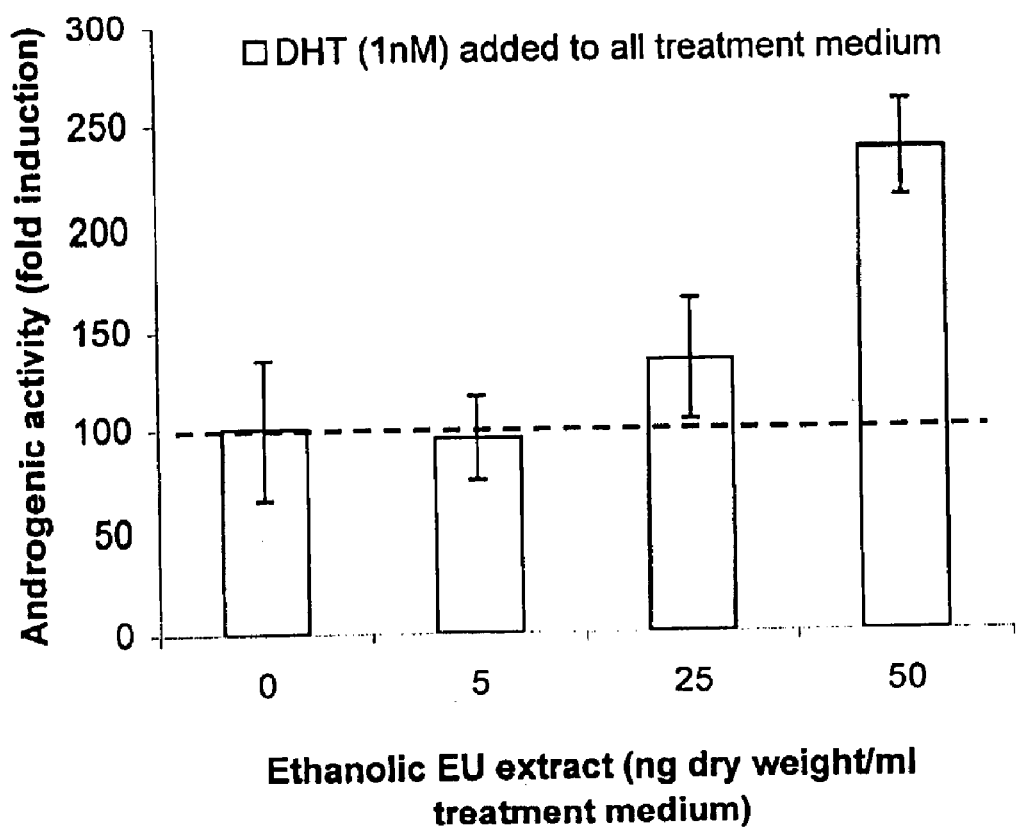

FIG. 1c—increasing doses of testosterone in the presence of 50 ng/ml of an ethanolic EU extract FIG. 1d—increasing doses of DHT in the presence of 50 ng/ml of an ethanolic EU extract FIG. 1e—increasing doses of an ethanolic EU extract in the presence of 1 nM DHT.

Experiments in HeLa cells were conducted as described in Example 2. As shown in FIG. 1a, ethanolic EU extract alone demonstrates intrinsic androgenic activity by increasing Luc activity to a maximal 1.87-fold in a dose-dependent manner. After 20% water precipitation of the ethanolic EU extract (=hydroethanolic EU extract), some phyto-metabolites that are cell inhibitory were removed, resulting in a more consistent dose-response curve with a maximal induction of over 6-fold (FIG. 1b). This shows that ethanolic extraction increases the concentration of the androgenic compound(s), and that further precipitation with water (ethanol/water, 80:20) will further enhance the steroidogenic activities of the ethanolic extract.

Most strikingly, an ethanolic EU extract can synergise and augment the effects of physiological androgens. In FIG. 1c, testosterone, at a dose of >1 nM, was able to induce maximal androgen receptor activity to about 100-fold higher than replicates not exposed to androgen. Addition of an ethanolic EU extract raised this maximum further to over 200-fold, an increase of about 100% compared to testosterone alone. This novel synergistic action on maximal androgen receptor activity was also evident with DHT. The presence of an ethanolic EU extract shifted upwards the maximum of the DHT dose-response curve by 40–60% (FIG. 1d). To further confirm this unprecedented synergistic bioactivity, increasing concentration of an ethanolic EU extract was added to DHT. As shown in FIG. 1e, an ethanolic EU extract dose-dependently raised androgen receptor activity above that observed with a saturating dose of DHT (1 nM).

EXAMPLE 4

Competitive Radioligand Displacement Bioassays

To demonstrate that the transactivation of the androgen receptor is due to the specific binding of the phyto-androgen (s) contained in an ethanolic EU extract, competitive radioligand displacement assays were carried out (Wilson, 1976). In this assay, androgen receptors expressed in COS-7 cells were simultaneously exposed to increasing concentrations of an ethanolic EU extract and a limiting amount (3 nM) of tritiated testosterone. The ability of an ethanolic EU extract to compete with radiolabelled testosterone for androgen receptor binding is compared to a strong androgen (DHT) and a non-ligand, cortisol. Thus, DHT and cortisol are positive and negative controls, respectively. The treated cells were harvested and the amount of tritiated testosterone bound to androgen receptor was measured by scintillation counting. Specific binding is expressed as percent tritium bound to androgen receptor, where 100% was the amount of specific tritiated-testosterone bound in the absence of competing cold ligand minus background (non-specific binding to substrate and proteins).

As shown in FIG. 2, an ethanolic EU extract competes well with tritiated testosterone, showing a graduated displacement of tritiated testosterone as the concentration of an ethanolic EU extract was increased, attaining 62.6% displacement at cf. 10. In contrast, the non-ligand cortisol does not displace tritiated testosterone at concentrations ranging from 0.3 to 10 nM. The androgen DHT also displaces tritiated testosterone in a dose-responsive pattern, attaining 92.4% displacement at 10 nM DHT. This demonstrates that the displacement of tritiated testosterone from androgen receptor is restricted to true androgen receptor ligands and an ethanolic EU extract that contain phyto-androgens that binds specifically to the ligand binding pocket of the androgen receptor LBD.

EXAMPLE 5

Estrogenic Activity in Herbal Extracts

The ethanolic EU extract was tested for estrogenic activity in HeLa cells cotransfected with an estrogen receptor expression plasmid and a luciferase-receptor plasmid containing estrogen responsive elements (ERE). In this assay the estroegnic activity of any added compound can be accurately measured. The results are shown in FIGS. 3 to 5. FIG. 3 shows that an ethanolic EU extract has estrogenic activity on its own as it can increase the response of the reporter gene to a maximum of 1.6-fold, compared to 4–6 fold for estradiol. FIG. 4 shows that the same extract can potentiate the effect of estradiol by doubling the activity of the reporter gene compared to estradiol alone. This synergistic activity of an ethanolic EU extract on estrogenic activity was also observed when increasing doses of ethanolic EU extract were co-incubated with 0.1 nM estradiol (FIG. 5).

The ability of the herbal extract to modulate estrogenic activity provides a method for conducting hormonal therapy in hypoestrogenic states such as menopause, osteoporosis and cardiovascular disease.

EXAMPLE 6

In-Vivo Androgen Modulatory Activity in Animal Studies

To determine the androgenic effect of an ethanolic EU extract in animals, the growth of the ventral prostate gland, an androgen-dependent tissue, in immature Wistar rats was measured. These immature rats have low levels of testosterone and consequently underdeveloped prostate tissue. In this model, exogenous androgen administration can be directly correlated with the growth of the ventral prostate. Thus, a dose-dependent increase in prostate weight (per unit body weight) can be observed when testosterone was administered intramuscularly (FIG. 6a). Administration of an ethanolic EU extract alone at doses from 1 mg to 10 mg also resulted in dose-dependent increments in prostatic weight (FIG. 6b).

Interestingly, the total androgenic effect of an ethanolic EU extract and testosterone was higher than that observed with high doses of testosterone alone. This novel ability of an ethanolic EU extract to increase prostatic growth to a level above that observed with maximal testosterone levels, was seen clearly in an experiment wherein animals were administered a high dose of testosterone (5000 ug) and also orally fed 50 mg of an ethanolic EU extract (FIG. 6c). These experiments indicate that an ethanolic EU extract was able to exert a synergistic effect on androgen action when administered orally, consistent with the synergistic effect observed in the cell studies shown in FIG. 1.

EXAMPLE 7

Solid Phase Separation of Compounds Exhibiting Steroidogenic Activity

In an effort to further define the composition of the bioactive compound(s) in an ethanolic EU extract with steroidogenic activity, we further separated the compounds using a solid phase extraction procedure. A Diol matrix was loaded into a glass column and an ethanolic EU extract was dry packed on top of the Diol matrix. Diol matrix is a polar sorbent that can exhibit both polar and weak non-polar interactions, the surface silanol groups are available for additional secondary polar interactions. Diol matrix consists of spherical particles of silica with Diol functions ($-(OH)_2$) at the end of hydrocarbon chains ($-CH_2-$). The hydrocarbon chains are attached to the silica particles by alkyl ether spacers.

The ethanolic EU extract was then sequentially eluted into individual fractions using the following solvents of increasing polarity in the following order: hexane 100%, hexane:DCM (1:1) 100%, DCM 100% and methanol 100%. The fractions were dried down in a rotary evaporator at 37° C. and then resuspended in ethanol for AR bioassay. It was observed that synergistic androgenic activity (with MB) was present in all the fractions, but with the most activity observed in the methanol 100% fraction. (FIG. 7a). Since methanol is a polar organic solvent, this indicates that one of the most androgenic compound(s) is an organic molecule of mixed polarity. It also indicates that the androgenic activity is likely to be the result of several compounds, as all fractions exhibited androgenic activity, albeit to a lesser degree than the methanol 100% fraction.

To further define the androgenic compounds, we used solvents of further defined polarity in the Diol matrix columns and studied their synergistic effects with the physiological androgen, DHT (FIG. 7b). We used the solvents DCM, ethyl acetate and ethanol (EtOH) as they cover the range of polarity shown to have the greatest activity in FIG. 7a. Synergistic androgenic activity eluted with the first fraction of ethanol (EtOH I), indicating that one class of active compound(s) is of relatively high polarity.

EXAMPLE 8

Thin Layer Chromatography (TLC) Separation of Steroidogenic Compounds

An ethanolic EU extract was loaded onto a Sephadex LH-20 column and eluted with n-butanol. Sephadex LH-20 matrix is a hydroxypropylated, cross-linked dextran matrix having an exclusion limit for peptides of 4 kilodaltons and an exclusion limit for small organic molecules of 5 kilodaltons and has dual lipophilic and hydrophilic properties. It is a crosslinked dextran gel that derives its lipophilic character from the isopropyl groups (—$CH_2$—CH—$CH_2$—) present. The hydrophilicity is due to the numerous hydroxyl functions present (—OH). Dextran (Dex) is a general term referring to linear highly polymeric carbohydrates arising as metabolic products of the bacterium *Leuconostoc mesenteroides* growing on a cane sugar substrate. Sephadex LH-20 matrix consists of Dex cross-linked via glycerol ether bridges.

The butanol eluate was further fractionated by two-dimensional thin layer chromatography (TLC). 100 ul of the butanol eluate was spotted band-wise on a TLC Silica Gel-60 glass plate at the baseline. The TLC plate was then developed in a chamber with 10 ml of the first solvent system, 100% dichloromethane. After 20 mins, the TLC plate was turned 90 degrees with respect to the first baseline and a second solvent system, 100% hexane was used to develop the 2-D TLC plate for 10 min. After the secondary exposure to 100% hexane, the TLC plate was air-dried at room temperature.

The TLC plate was then visualized under UV illumination. Multiple fluorescent bands of different colors such as blue and yellow were seen spread between baseline ('B0', $R_f=0$) to a point 'B1', having an $R_f$ of 0.4. The most prominent bands visible under UV were found at 'B0' and 'B1'.

Subsequently, the TLC plate was chemically reacted with a vanillin-sulphuric acid spray and the plate baked at 90° C. for 30 min. This time, various hues of violet-blue bands and brown bands were seen distributed between 'B0' to 'end'. The most prominent of these bands were marked as 'B2', 'B3', 'B4' and 'end' with corresponding $R_f$ values are 0.47, 0.62, 0.71 and 1 respectively.

A composition of the invention is preferably one that lacks at least one of the components B0, B1, B2, B3, B4 and "end", as these represent compounds that are not bioactive according to the present invention.

The bands and regions between those bands that were visualized by UV and vanillin-sulphuric acid reagent (i.e. the 'interbands') were then scraped off as silica gel-60 powders from another intact duplicate TLC plate based on the $R_f$ values. The original TLC plate used for the vanillin-sulphuric acid reaction cannot be re-used for further analyses as the vanillin-sulphuric acid chemical reaction is a destructive process.

After the silica gel-60 powders containing the TLC bands and 'interbands' were scraped off, they were then individually incubated at 37° C. for 12 hours in 10 ml aliquot of 100% ethanol in separate centrifuge tubes to elute the EU compounds into solution for the bioassays.

FIG. 8 shows that a largely hydrophobic n-butanolic fraction, obtained by passing an ethanolic EU extract through a Sephadex LH-20 column, can be further differentiated into bands of phytocompounds that possess subtle differences in hydrophilicity based on hydrophilic interaction with the silanol groups of the silica gel stationary phase of a thin layer chromatography (TLC) plate. This shows that the AR agonist activity of an ethanolic EU extract is found in more than one single compound. Also, the bioactive compounds possess mixed polarities based on the Sephadex LH-20 and TLC chromatographic separations. A (non-limiting) example of a mixed polarity compound would be a saponin (with a steroidal or triterpenoid aglycone coupled to sugar moieties); or a flavonoid with conjugated hydrophobic aromatic ring structures carrying entities such as hydrophilic hydroxyl or amide side-groups; or an Okadaic acid-type conjugated ring structure system with charged side-groups such as (but not restricted to) methyl, hydroxyl or amide groups; or fatty-acids derivatives and/or conjugates such as lipopolysaccharides (LPS).

EXAMPLE 9

High Performance Liquid Chromatography (HPLC) Separation of Steroidogenic Compounds 10 mg of dried EU ethanolic extract was dissolved in 2 ml of acetonitrile and applied to a C-18 reverse phase HPLC column. The chromatographic mobile phase consists of acetonitrile and water in the following percentages:

| Flow type | Duration (min) | Percentage acetonitrile to water in the mobile phase |
|---|---|---|
| Isocratic | 0–15 | 10% acetonitrile |
| Gradient | 15–40 | 10% to 50% acetonitrile |
| Gradient | 40–60 | 50% to 100% acetonitrile |
| Isocratic | 60–100 | 100% acetonitrile |
| Gradient | 100–120 | 100% to 10% acetonitrile |

Fractions F1, F2 and F3 are broad time-based fractions. F1 was collected from 40 min to 60 min, F2 was collected from 60 min to 80 min and F3 was collected from 80 min to 120 min.

FIG. 9 indicates that the androgenic activity of an ethanolic EU extract can be separated into different fractions with varying degree of agonistic and androgen-boosting effects. This shows that the androgenic/booster bioactivities of an ethanolic EU extract are mediated by different classes of phytocompounds which can be separated on a reverse phase C-18 matrix. The hydrophobic stationary reverse phase (C-18) matrix was able to interact with and resolve the ethanolic EU extract into three fractions with differing bioactivating characteristics. This demonstrates that the active molecules responsible for androgenic and androgen-boosting bioactivity are of different polarities with at least some hydrophobic moieties and/or different type(s) of chemical structures. In other words, an ethanolic EU extract contains more than one compound having biological action on the AR.

The elution profiles of three experiments are superimposed in FIG. 10. Two major peaks can be identified in fraction F2, having retentions times of 61.6 minutes and 64 minutes, respectively.

EXAMPLE 10

Combination Chromatographic Separation of Active Compounds

The chromatographic approaches to separating steroidogenic compounds according to the invention, especially those compounds having a synergistic action with steroids, preferably with androgens and estrogens, can be applied in combination to obtain more purified fractions. One preferred combination is to obtain an alcoholic eluate from a diol column and apply that eluate to a reverse phase column. In an example of this approach, an ethanol, hexane or DCM extract of EU is applied to a diol column by dry packing and then the diol column is eluted with DCM followed by ethyl acetate then by ethanol. The ethanol eluate is collected and applied to a reverse phase C-18 column (either directly or by dry packing). The reverse phase column is eluted with an isocratic mobile phase of methanol:water (1:1 by volume) followed by 100% methanol, then followed by 100% DCM. The DCM eluate is collected as the active fraction. Three column volumes of mobile phase are used for each elution step for both columns.

EXAMPLE 11

Effective Dosage in Humans

Those skilled in the art, will recognize that the examples described above allow a prediction of the dose that will be effective in humans. The in vitro cell culture experiments indicate that synergistic activity can be observed at doses ranging from 0.05 ng/ml to 500 ng/ml of the ethanolic EU extract or hydroethanolic EU extract. Since the human blood volume is 5000 mls, it is anticipated that assuming 100% absorption, a dose of 0.25 μg to 2.5 mg of dried ethanolic EU extract or hydroethanolic EU extract can be effective. Animal studies indicate that 1 mg/200 g to 50 mg/200 g body weight of dried ethanolic EU extract administered orally exhibits androgenic effect. Assuming that the average male weighs 70 kg, the effective oral dose per weight basis would range from 350 mg to 17.5 g of dried ethanolic EU extract. Such a dose would be administered at least once every other day, preferably one, two, three or four times per day.

A protocol for clinical trial of the extract of the invention has been submitted. In the trial, dried EU extract of the invention will be formulated into capsules for oral administration to subjects in doses from 500 to 3000 mg, administered two or three times per day.

Patients: 21 to 30 males with primary hypogonadism, aged 20 to 60 years, with serum testosterone levels below the normal range (testosterone <5 ng/ml) and raised serum gonadotrophins (FSH and LH >7 IU/L) but who are otherwise healthy.

Primary Endpoint Measures

The main outcome measure will be significant suppression of gonadotrophins (FSH and LH) to 60% of baseline levels; return to normal levels is desired. Secondary outcome measures will be androgenic-regulated changes in SHBG, HDL-cholesterol, hemoglobin and prostate specific antigen levels. Return of these physiologic parameters to normal levels is desired.

Other outcome measures for subsequent trials (applicable for both men and women) include psychometric indices of sexual function/libido and mood/feelings; dual energy X-ray absorptiometry (DEXA) and/or magnetic resonance imaging (MRI) measurements of body proportions of fat, lean body mass, muscle bulk distribution and bone mineral density; dermatologic evaluation for hydration, pigmentation and sebum production in skin. FSH and LH suppression are also applicable for women.

TABLE 1[1]

Table 1a Androgenic activity of herbal extracts

| Herbal extract | Androgenic activity (fold induction) | (%) percentage of 1 nM DHT activity |
|---|---|---|

TABLE 1[1]-continued

| Ethanolic EU extract | 41 | 7.8 |
| P. ginseng | 1.9 | 0.4 |
| P. quinquefolius | 1.7 | 0.3 |
| Jamu Tongkat Ali | 1.2 | 0.2 |

Table 1b Androgenic activity of herbal extracts in the presence of DHT (1 nM).

| Herb | Herbal extract + DHT (Androgenic activity fold induction) | DHT alone (Androgenic activity fold induction) | Ratio (%) (Herbal extract + DHT/DHT alone) |
|---|---|---|---|
| SB | 29 | 183 | 15.8 |
| SE | 162 | 183 | 88.5 |
| SY | 175 | 183 | 95.6 |
| SZ | 187 | 183 | 102 |
| Ethanolic EU extract | 403 | 215[2] | 187 |

Table 1c Absence of transactivation activity of ethanolic EU extract with progesterone and glucocorticoid receptors

| Treatment | Luc activity (fold induction) | Ratio of Luc activity as percentage (%) of 1 nM ligand |
|---|---|---|
| Ethanolic EU extract + progesterone receptor | 1.3 | 1.9 |
| Ethanolic EU extract + progesterone + progesterone receptor | 43 | 64 |
| Progesterone + progesterone receptor | 67 | 100 |
| Ethanolic EU extract + glucocortcoid receptor | 2.2 | 1.1 |
| Ethanolic EU extract + cortisol + glucocortcoid receptor | 192 | 99 |
| Cortisol + glucocortcoid receptor | 194 | 100 |

[1]Wild type androgen receptor was transiently expressed in HeLa cells and exposed to 1 nM DHT or 50 ng/ml herbal extracts (Table 1a). HeLa cells were exposed to 1 nM DHT in the presence of different herbal extracts (Table 1b). Ethanolic EU extracts tested for progesterone and glucocorticoid activity (Table 1c). Transactivation activity was measured with an androgen-regulated reporter gene, ARE-Tata-Luc and expressed as fold increase in luciferaseactivity compared with cells not exposed to androgen or herbal extract. Progesterone or glucocorticoid receptors were utilized when testing for progestogenic or glucocorticoid activities respectively. Each data point is the mean of triplicate samples.
[2]Difference in DHT androgenic activity compared to that of other herbs is because the ethanolic EU extract assay was performed on a different day.
[3]Fold increase in luciferase reporter gene activity coupled to appropriate hormone response element, compared to wells not exposed to hormone or herbal extract. Cells were exposed to 1 nM of either progesterone or cortisol.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Various articles of the scientific and patent literature are cited throughout this paper. Each such article is hereby incorporated by reference in its entirety and for all purposes by such citation.

BIBLIOGRAPHY

1. Dowsing et al. (1999) Lancet 354:640–643.
2. Ghadessy et al. (1999) J. Clin. Invest. 103:1517–25 Li, S. Z. (1987) "Ben Cao Gang Mu" Ren Min Wei Sheng Chu Ban She, Beijing, 1986–1987.

3. Li et al. (1999a) *Biol. Pharm. Bull* 22:582–585.
4. Li et al. (1999b) *Bio. Pharm. Bull.* 22:941–946
5. Lim et al. (1997) *Mol. Cell Endrocinol.* 131:205–2210.
6. Nakamura et al. (1997) *Mutat. Res.* 388:7–20.
7. Ong et al. (1999) *Lancet* 354:1444–1445.
8. Quigley et al. (1995) *Endocr Rev.* 16:271–321.
9. Tut et al. (1997) *J. Clin. Endocrinol. Metab.* 82:3777–3782.
10. Wang et al. (1998) *Clin. Genet.* 54:185–192.
11. Wei et al. (1955) *"Shen Nong Ben Cao Jing"*, Shang Wu Yin Shu Guan, Beijing p. 43.
12. Wilson, E. M. and French, F. S. (1976) *J. Biol. Chem.* 251:5620–5629.
13. Wilson, J. (1992) Androgens. In: eds. Gilman A. G, Rall T. W. Nies A. S., Taylor P. *"The pharmacological basis of therapeutics"*, 8th Edition. McGraw Hill, Singapore, 1413–1430.
14. Yong et al. (1994), *Lancet* 344(8925):826–827.
15. Yong et al. (1998) *Mol. Cell Endocrinol.* 137:41–50.
16. Jenster et al. (1997) *Proc. Natl. Acad. Sci. USA* 94:7879–7884.

What is claimed is:

1. A composition comprising:
   a preparation of *Eucommia ulmoides* prepared by ethanol extraction thereof and chromatography a) over a hydroxypropylated, cross-linked dextran matrix having an exclusion limit for peptides of 4 kilodaltons and an exclusion limit for small organic molecules of 5 kilodaltons with elution using n-butanol or b) over a reverse phase matrix with elution by an aqueous buffer and acetonitrile gradient or c) over a diol matrix with elution using at least one organic solvent;
   that lacks fluorescent components exhibiting $R_f$ values of 0 and 0.4 and also lacks vanillin-sulphuric acid reactive components exhibiting $R_f$ values 0.47, 0.62, 0.71 and 1 when the composition is separated by two dimensional thin layer chromatography on silica gel and eluted in the first dimension with dichloromethane and in the second dimension with hexane.

2. The composition of claim 1, wherein the preparation comprises at least one flavonoid compound.

3. The composition of claim 1, wherein the preparation comprises at least one saponin compound.

4. The composition of claim 1, wherein the preparation comprises at least one compound comprising an okadaic acid-type conjugated ring structure.

5. The composition of claim 1, wherein the preparation comprises at least one compound comprising a fatty acid.

6. The composition of claim 1, wherein the preparation comprises at least one saponin compound and at least one flavonoid compound.

7. The composition of claim 1, further comprising at least one pharmaceutically acceptable carrier or diluent.

8. A method of modulating a steroid-mediated physiological condition in a subject, said method comprising administering to said subject an amount of the composition of claim 1
   that is effective for modulating the steroid-mediated physiological condition in the subject.

9. The method according to claim 8, wherein the composition is administered to a human, a primate or a livestock animal.

10. The method according to claim 9 wherein the steroid-mediated physiological condition is mediated by an androgen or by androgen receptor.

11. The method according to claim 9, wherein the steroid-mediated physiological condition is male sexual development, secondary sexual development, anabolic processes, male sex drive, skin condition, hair growth, physical stamina or lipid metabolism.

12. The method according to claim 9, wherein the steroid-mediated physiological condition is mediated by estrogen or estrogen receptor.

13. The method according to claim 9, wherein the steroid-mediated condition is menopause, osteoporosis, cardiovascular disease or other estrogen-related disease or process.

14. An article of manufacture comprising the composition according to claim 1 and written material that provides instructions or urges the use of the composition to modulate, a physiological condition or response mediated by a steroid.

15. The composition of claim 1, wherein said preparation produces a two-fold or greater increase in the activation of a liganded androgen receptor.

16. The composition of claim 1, wherein said preparation produces a two-fold or greater increase in the activation of a liganded estrogen receptor.

17. The composition of claim 1, wherein said preparation produces an agonist effect on an unliganded androgen receptor.

18. The composition of claim 1, wherein said preparation produces an agonist effect on an unliganded estrogen receptor.

* * * * *